(12) United States Patent
Xing et al.

(10) Patent No.: US 9,707,294 B2
(45) Date of Patent: Jul. 18, 2017

(54) TRANSFECTION WITH MAGNETIC NANOPARTICLES

(71) Applicant: IntellengentNano Inc., Edmonton (CA)

(72) Inventors: James Xing, Edmonton (CA); Jie Chen, Edmonton (CA)

(73) Assignee: Hidaca Limited, Calgary, Alberta (CA)

( * ) Notice: Subject to any disclaimer, the term of this patent is extended or adjusted under 35 U.S.C. 154(b) by 0 days.

(21) Appl. No.: 14/698,676

(22) Filed: Apr. 28, 2015

(65) Prior Publication Data

US 2015/0344869 A1    Dec. 3, 2015

Related U.S. Application Data

(63) Continuation of application No. 13/440,647, filed on Apr. 5, 2012, now Pat. No. 9,339,539, which is a continuation-in-part of application No. 13/127,259, filed as application No. PCT/CA2009/001629 on Nov. 9, 2009, now abandoned.

(60) Provisional application No. 61/112,451, filed on Nov. 7, 2008.

(51) Int. Cl.
  *C12N 13/00* (2006.01)
  *C12N 15/87* (2006.01)
  *A61K 41/00* (2006.01)
  *B82Y 5/00* (2011.01)

(52) U.S. Cl.
  CPC ...... *A61K 41/0047* (2013.01); *A61K 41/0028* (2013.01); *A61K 41/0052* (2013.01); *B82Y 5/00* (2013.01); *C12N 13/00* (2013.01); *C12N 15/87* (2013.01)

(58) Field of Classification Search
  None
  See application file for complete search history.

(56) References Cited

U.S. PATENT DOCUMENTS

| | | | |
|---|---|---|---|
| 9,339,539 B2 | 5/2016 | Xing et al. | |
| 2007/0196281 A1 | 8/2007 | Jin et al. | |
| 2007/0231908 A1 | 10/2007 | Cai et al. | |
| 2009/0104700 A1* | 4/2009 | Samuel | C12N 15/8207 435/412 |
| 2010/0273673 A1 | 10/2010 | Kim et al. | |
| 2010/0311168 A1 | 12/2010 | Samuel et al. | |
| 2011/0251547 A1 | 10/2011 | Xing et al. | |

FOREIGN PATENT DOCUMENTS

| | | | |
|---|---|---|---|
| WO | 2007/015179 | 2/2007 | |
| WO | WO 2007/015179 | * 2/2007 | ............ A61N 1/406 |
| WO | 2010/051643 | 5/2010 | |

OTHER PUBLICATIONS

Mehier-Humber et al., Physical methods for gene transfer: Improving the kinetics of gene delivery into cells, Advanced Drug Delivery Reviews, 57 (2005) 733-753.*
Xu et al., Inorganic nanoparticles as carriers for efficient cellular delivery, Chemical Engineering Science, 61 (2006) 1027-1040.*
Torney et al., Mesoporous silica nanoparticles deliver DNA and chemicals into plants, Nature Nanotechnology, vol. 2, May 2007, 295-300.*
Herranz et al., The Application of Nanoparticles in Gene Therapy and Magnetic Resonance Imaging, Microsc Res Tech., Jul. 2011; 74(7): 577-591.*
WO PCT/CA2009-001629, mailed Feb. 9, 2010, 4 pages.
WO PCT/CA2009-001629, mailed May 19, 2011, 12 pages.
U.S. Appl. No. 13/127,259, mailed Apr. 9, 2013, 12 pages.
U.S. Appl. No. 13/440,647, mailed Apr. 8, 2013, 12 pages.
U.S. Appl. No. 13/440,647, mailed Dec. 24, 2013, 8 pages.
U.S. Appl. No. 13/440,647, mailed Mar. 13, 2014, 3 pages.
U.S. Appl. No. 13/440,647, mailed Jul. 23, 2014, 13 pages.
U.S. Appl. No. 13/440,647, mailed Jan. 8, 2015, 5 pages.
U.S. Appl. No. 13/440,647, mailed May 14, 2015, 12 pages.
U.S. Appl. No. 13/440,647, mailed Jul. 29, 2015, 12 pages.
U.S. Appl. No. 13/440,647, filed Apr. 5, 2012.
Hao, Y. et al., "Magnetic gold nanoparticles as a vehicle for fluorescein isothiocyanate and DNA delivery into plant cells", Botany, vol. 91, pp. 457-466, (2013).
Hao, Y. et al., "FITC delivery into plant cells using magnetic single-walled carbon nanotubes", Journal of Nanoscience and Nanotechnology, vol. 12, pp. 1-7, (2012).
Scherer, F. et al., "Magnetofection: enhancing and targeting gene delivery by magnetic force in vitro and in vivo", Gene Therapy, vol. 9 pp. 102-109, (2002).
www.Magnet4less.com, 13 pages, downloaded on Dec. 9, 2014.
International Search Report dated Feb. 9, 2010 for PCT application No. PCT/CA2009/001629, 3 pages.
King, R. "Gene delivery to mammalian cells by microinjection", Methods in Molecular Biology, vol. 245, Gene Delivery to Mammalian Cells: vol. 1 : Nonviral Gene Transfer Techniques, pp. 167-173, (2004).
Helenius, E. et al., "Gene delivery into intact plants using the Helios™ gene gun", Plant Molecular Biology Reporter, vol. 18, issue 3, pp. 287a-287l, (2000).
Van Tendeloo, V.F.I. et al., "Highly efficient gene delivery by mRNA electroporation in human hematopoietic cells: superiority to lipofection and passive pulsing of mRNA and to electroporation of plasmid cDNA for tumor antigen loading of dendritic cells", Blood, vol. 98, No. 1, pp. 49-56, (2001).

(Continued)

*Primary Examiner* — Karen Cochrane Carlson
*Assistant Examiner* — Jennifer M. H. Tichy
(74) *Attorney, Agent, or Firm* — Evan Law Group LLC

(57) ABSTRACT

The invention includes a magnetic nanoparticle molecular delivery vehicle to be used for transfection and delivery of therapeutic molecules across cell membranes and to specific sites in the body, using magnetic forces and ultrasound.

10 Claims, 35 Drawing Sheets

(56) References Cited

OTHER PUBLICATIONS

Pan, H. et al., "Sonoporation of cells for drug and gene delivery", Proceedings of the 26th Annual International Conference of the IEEE EMBS, San Francisco, CA, pp. 3531-3534, Sep. 1-5, 2004.

Watson, A. et al., "Gene delivery into neuronal cells by calcium phosphate-mediated transfection", Methods: A companion to Methods in Enzymology, vol. 10, article No. 0105, pp. 289-291, (1996).

Beattie, S.G. et al., "Recombinant adeno-associated virus-mediated gene delivery of long chain acyl coenzyme A dehydrogenase (LCAD) into LCAD-deficient mice", The Journal of Gene Medicine, vol. 10, pp. 1113-1123, (2008).

Bettinger, T, et al., "Peptide-mediated RNA delivery: a novel approach for enhanced transfection of primary and post-mitotic cells", Nucleic Acids Research, vol. 29, No. 18, pp. 3882-3891, (2001).

Liu, Z. et al., "Supramolecular stacking of doxorubicin on carbon nanotubes for in vivo cancer therapy", Angewandte Chemie International Edition, vol. 48, issue 41, pp. 7668-7672, (2009).

Bianco, A. et al., "Biomedical applications of functionalized carbon nanotubes", Chemical Communications, vol. 5, pp. 571-577, (2005).

Sakakima, Y. et al., "Gene therapy for hepatocellular carcinoma using sonoporation enhanced by contrast agents", Cancer Gene Therapy, vol. 12, pp. 884-889, (2005).

Baque, P. et al., "Naked DNA injection for liver metastases treatment in rats", Hepatology, vol. 35, No. 5, pp. 1144-1152, (2002).

Yamashita, Y-I. et al., "In vivo gene transfer into muscle via electro-sonoporation", Human Gene Therapy, vol. 13, No. 17, pp. 2079-2084, (2002).

Miller, M.W. et al., "A review of in vitro bioeffects of inertial ultrasonic cavitation from a mechanistic perspective", Ultrasound in Medicine & Biology, vol. 22, No. 9, pp. 1131-1154, (1996).

Newman, C.M.H. et al., "Gene therapy progress and prospects: Ultrasound for gene transfer", Gene Therapy, vol. 14, pp. 465-475, (2007).

Dalecki, D. et al., "Ultrasonically induced lung hemorrhage in young swine", Ultrasound in Medicine & Biology, vol. 23, No. 5, pp. 777-781, (1997).

Huber, P.E. et al., "In vitro and in vivo transfection of plasmid DNA in the Dunning prostate tumor R3327-AT1 is enhanced by focused ultrasound", Gene Therapy, vol. 7, No. 17, pp. 1516-1525, (2000).

Liang, H-D. et al., "Optimisation of ultrasound-mediated gene transfer (sonoporation) in skeletal muscle cells", Ultrasound in Medicine & Biology, vol. 30, No. 11, pp. 1523-1529, (2004).

Mehier-Humbet, S. et al., "Physical methods for gene transfer: Improving the kinetics of gene delivery into cells", Advanced Drug Delivery Reviews, vol. 57, pp. 733-753, (2005).

Xu et al., "Inorganic nanoparticles as carriers for efficient cellular delivery", Chemical Engineering Science, vol. 61, pp. 1027-1040, (2006).

Torney et al., "Mesoporous silica nanoparticles deliver DNA and chemicals into plants", Nature Nanotechnology, vol. 2, pp. 295-300, (2007).

Kaminski, M.D. et al., "Encapsulation and release of plasminogen activator from biodegradable magnetic microcarriers", European Journal of Pharmaceutical Sciences. vol. 35, pp. 96-103, (2008).

Larina, I.V. et al., "Enhancement of drug delivery in tumors by using interaction of nanoparticles with ultrasound radiation", Technology in Cancer Research and Treatment, vol. 4, No. 2, pp. 217-226, (2005).

Stride, E. et al., "Enhancement of microbubble mediated gene delivery by simultaneous exposure to ultrasonic and magnetic fields", Ultrasound in Medicine and Biology, vol. 35, No. 5, pp. 861-868, (2009).

Dobson, J. "Gene therapy progress and prospects: magnetic nanoparticle-based gene delivery", Gene Therapy, vol. 13, pp. 283-287, (2006).

McBain, S.C. et al. "Magnetic nanoparticles as gene delivery agents: enhanced transfection in the presence of oscillating magnet arrays", Nanotechnology, vol. 19, pp. 1-5, (2008).

Husseini, G.A. et al., "Micelles and nanoparticles for ultrasonic drug and gene delivery", Advanced Drug Delivery Reviews, vol. 60, pp. 1137-1152, (2008).

Hao, Y. et al., "Magnetic gold nanoparticles: Synthesis, characterization, and its application in the delivery of FITC into KG-1 cells", Journal of Nanoscience and Nanotechnology, vol. 12, No. 10, pp. 7716-7722, (2012).

Gul-Uludag, H. et al., "Efficient and rapid uptake of magnetic carbon nanotubes into human monocytic cells: implications for cell-based cancer gene therapy", Biotechnology Letters, vol. 34, pp. 989-993, (2012).

Hao, Y. et al., "Impact of carbondiimide crosslinker used for magnetic carbon nanotube mediated GFP plasmid delivery" Nanotechnology, vol. 22, pp. 1-9, (2011).

Hao, Y. et al., "Exploring the cell uptake mechanism of phospholipid and polyethylene glycol coated gold nanoparticles", Nanotechnology, vol. 23, pp. 1-8, (2012).

Gul, H. et al., "Magnetic carbon nanotube labelling for haematopoietic stem/progenitor cell tracking", Nanotechnology, vol. 21, pp. 1-9, (2010).

He, C. et al., "A new purification method for carbon nanotubes and associated atomic force microscope force-distance curve analysis", Separation and Purification Technology, vol. 81, pp. 174-183, (2011).

Merriam-Webster Dictionary, Protoplast, Accessed Jul. 24, 2015, Online at: Merriam-webster.com/dictionary/protoplast.

Shubayev, V.I. et al., "Magnetic nanoparticles for theragnostics", Advanced Drug Delivery Reviews, vol. 61, pp. 467-477, (2009).

* cited by examiner (Color) Control.
Blue: Nucleus
Green: GFP (Color) CNT-GFP (3 min incubation, 7 min applied magnetic field afterwards)
Blue: Nucleus
Green: GFP (Color) Control cells.
Blue: Nucleus.
Red: Cell membrane.

(Color) SWNT 5 delivered cells. After SWNT 5 carrier exposure, FITCs are distributed in cytoplasm and even inside nucleus (green colored dots pointed by arrows).

(a) Control     (b) Biodegradable-tube + GFP

TRANSFECTION WITH MAGNETIC NANOPARTICLES

CROSS-REFERENCE TO RELATED APPLICATIONS

This application is filed under 37 CFR 1.53(b) as a continuation-in-part application. This application claims priority under 35 USC §120 of U.S. patent application Ser. No. 13/127,259 filed on May 3, 2011, and which is the U.S. National Stage of International Application No. PCT/CA2009/001629, filed Nov. 9, 2009, which designates the U.S., published in English, and which claims the benefit of U.S. Provisional Application No. 61/112,451, filed Nov. 7, 2008, the specifications of which are hereby incorporated by reference.

FIELD OF THE INVENTION

This invention relates to a nanostructured molecular delivery vehicle for delivering molecules to a selected site, and a method for transporting the molecular delivery vehicle across a biological membrane by applying a magnetic force and ultrasound.

BACKGROUND OF THE INVENTION

Transfection is the introduction of foreign material into eukaryotic cells using a vector as a means of transfer. The term transfection is most often used in reference to mammalian cells, while the term transformation is preferred to describe DNA transfer in bacteria and non-animal eukaryotic cells such as fungi, algae and plants.

Existing methods of transfection must overcome problems with the permeability of the cell membrane and the solubility of the transfected particle.

Drug delivery often involves transportation of the drug across cell membranes. The most basic method in vivo method is to introduce the drug into the blood stream by oral or intravenous methods and then hope it is absorbed by the correct cells. This non-discriminatory technique requires relatively large doses of the drug and simply does not work for some molecules such as DNA, which is used in gene therapy.

Existing methods to transfect material into a cell can be grouped into two categories: viral and non-viral. The utilization of viruses to transfect material into a cell has been shown to be extremely efficient; however, the possibility of a immune response to viruses and the insertion of mutagens into the body have proven to be serious concerns, especially in clinical trials. Non-viral drug delivery methods include naked DNA injection and electroporation. Unfortunately, naked plasmid DNA injection has shown to have a relatively low efficiency of gene delivery, while following electroporation tissue damage caused by the electric pulses has been observed.

Microinjection is a mechanical technique that utilizes a precision tool to place the molecule directly into the cell. This works excellently for DNA, however it is impractical in many situations as it can only be applied to one cell at a time.

A gene gun is a mechanical device that fires a particle bonded to the bio-molecule into the cell. These particles are relatively large and often damage cells. They also require large doses to be effective.

Electroporation is a physical method, which creates pores in the cell membrane by applying an electric shock to the cell. These pores allow the increased diffusion of materials into the cell. This increased permeability allows for easier transfection.

Sonoporation is similar to electroporation except it uses ultrasound to stimulate the cell membrane. The ultrasound also creates turbulence in the fluid surrounding the cell, which increases the rate of diffusion across the membrane.

Calcium phosphate transfection is a chemical method, which is very cheap. It uses calcium phosphate bonded to DNA. This molecule in some cases is able to transfect cells; however, this method is often ineffective and limited.

Viral delivery is a very effective method because viruses naturally are a carrier of genetic information and are very adept at entering cells. This makes them an obvious choice to help deliver DNA molecules into cells. However, the use of viral vectors is sometimes undesirable because of their immunogenicity and their potential mutagenicity. Furthermore, viral delivery is non-specific and can trigger side effects in the host.

Yet another method uses magnetic force and a molecular delivery vehicle to cross the cell membrane. A version of this method is described in United States Patent Application 2007/0231908 A1, and requires that the molecular delivery vehicle be oriented before it penetrates the biological membrane.

For most of the above methods, the effectiveness is extremely variable depending on the cell type being transfected. Some cells are known to be harder to transfect then others and these are usually the cells that hold the greatest reward.

Therefore, there is a need in the art for methods of transporting biomolecules and other molecules of interest into cells which mitigate the difficulties of the prior art.

SUMMARY OF THE INVENTION

The present invention provides for transfection of cells using nanoparticles and magnetic forces to direct the nanoparticles through a cell wall or membrane. In one embodiment, the nanoparticle is directed through a cell membrane, a nuclear membrane, or a cell membrane in vivo such as the blood-brain barrier. In one embodiment, the invention further comprises the use of ultrasound to increase the permeability of the biological membranes. This results in greater efficiency or molecular delivery or transfection.

This invention comprises the following aspects (a) a method of creating nanoparticles, which are nontoxic, magnetic, and bondable to biological molecules or other molecules of interest; (b) a method of bonding such molecules to this nanoparticle; and (c) a system to force these nanoparticles through a membrane using a magnetic field. In one embodiment, ultrasound in the form of low-intensity pulsed ultrasound (LIPUS) is used increase the permeability of the membrane.

In one aspect, the invention comprises a method of delivering a molecule across a cell membrane using a delivery vehicle comprising a magnetic nanoparticle, the method comprising the steps of:

(a) fixing the molecule to the nanoparticle;
(b) positioning the nanoparticle in the immediate vicinity of the cell membrane;
(c) subjecting the nanoparticle and cell membrane magnetic field; and
(d) simultaneously subjecting the nanoparticle and cell membrane to ultrasound.

The nanoparticle comprises bonding sites so that the molecule can be attached to this nanoparticle. The number of bonding sites is variable as is the spacing between bonding sites. In addition, the type of bond may be covalent, ionic or another bond which is capable of fixing the molecule to the nanoparticle. In one embodiment, the molecule may comprise a genetic material such as DNA or RNA, proteins, or any other biological molecule.

The nanoparticle may comprise nanotubes, such as carbon nanotubes, or single-walled carbon nanotubes. In one embodiment, the nanoparticles may be biodegradable or biocompatible, and may comprise silica. The nanoparticles may display low or no toxicity to cells in vivo or in vitro.

On a macroscopic scale, this magnetic force can be used to control the molecular delivery vehicles to move to certain parts of a body. On a microscopic to nanoscale level, this force can be used to force the molecular delivery vehicles through a biological membrane. If necessary or desired, the molecular delivery vehicle can be further transported into the nucleus of the cell by moving it with a magnetic force.

This membrane may be the cell wall or the wall of the nucleus inside the cell, or another biological membrane such as the mitochondrion's double membrane. This membrane could also be the blood-brain barrier. Thus, this invention may allow for the transportation of molecules into the central nervous system.

Thus using this method, a bio-molecule can be delivered to a specific target.

In one embodiment, the invention comprises a molecular delivery vehicle which comprises a nanostructure which is magnetic and has bonding sites so that a bio-molecule can be attached to this molecular delivery vehicle. The number of bonding sites is variable as is the spacing between bonding sites. In addition, the type of bond may be covalent, ionic or another bond which is capable of holding the biomolecule.

Using this magnetic force the magnetic nanoparticle can be controlled in numerous ways. In one embodiment, the delivery vehicles can be collected in one location using a magnetic force that attracts to that location, such as an organ or specific tissue in vivo.

In one aspect, the invention comprises a method for using the molecular delivery system to deliver molecules into cells or transfect such cells in vitro or in vivo. In vitro cells may be supported on solid or liquid media.

In one embodiment, the cell membrane may be from a cell chosen from a mammalian cell and a plant cell. The mammalian cell may be chosen from a normal cell or a cancer cell.

The plant cell may further comprise a cell wall.

The plant cell may be chosen from a canola cell or a carrot cell.

The cancer cell may be chosen from a MCF-7 cell, a HeLa cell, a KG-1 cell, a breast cancer cell, a cervic cancer cell, and a human acute leukemia cell.

The magnetic nanoparticle may be chosen from a magnetic gold nanoparticle (mGNP), a magnetic single wall carbon nanotube (mSWCNT), or combinations thereof.

BRIEF DESCRIPTION OF THE DRAWINGS

In order that the above-recited and other features and advantages of the present invention will be readily understood, a more particular description of the invention is given. Specific examples thereof are detailed, the result of which are illustrated in the appended figures. Any example is only a single embodiment of the invention, and is not to be considered in any way the limit of its scope. In the accompanying figures:

FIG. 13(a)—DNA plasmid concentration: 2 µg/mL, marker: MI, % Gated: 16.20. FIG. 13(b)—DNA plasmid concentration: 15 µg/mL, marker: MI, % Gated: 26.93. FIG. 13(c)—DNA plasmid concentration: 30 µg/mL, marker: MI, % Gated: 32.51. A high amount of cell viability is seen in all cases.

DETAILED DESCRIPTION OF THE PREFERRED EMBODIMENTS

This invention comprises a method to deliver biomolecules or other molecules of interest into cells using a molecular delivery vehicle, which is magnetically drivable and capable of bonding to at least one bio-molecule. This molecular delivery vehicle can pass through the cell wall with the aid of an external magnetic force.

"Biomolecule"—a biological molecule that performs some function which influences the behavior or nature of a biological system.

"Magnetic nanoparticle"—any particle on the nanoscale (having one dimension less than about 100 nm) the motion of which is influenced by a magnetic field.

"Nanoscale"—the range of lengths used to measure objects from 0.1 nm up to 1000 nm where 1 nm is $10^{-9}$ meters.

"Transfect"—a process to introduce foreign material into a cell.

The present invention relates to the use of magnetic nanoparticles to transport biomolecules and other molecules of interest across a cell membrane.

Figure 1A:
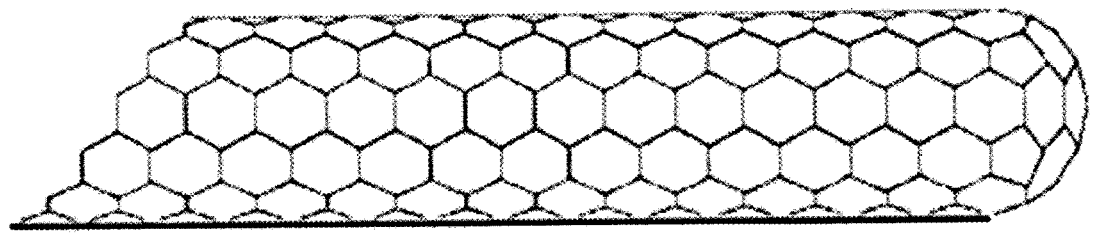
FIG. 1A is a sketch of a magnetic single walled nanotube and FIG. 1B is a sketch of a spherical magnetic nanoparticle after it has been functionalized.
Figure 1B:
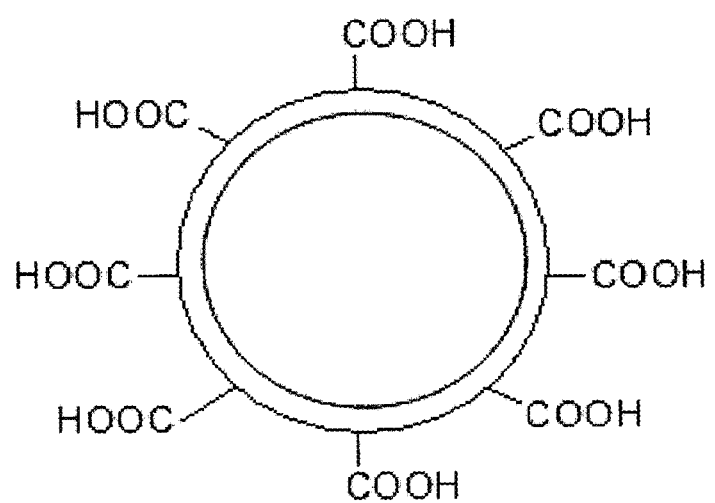

In one embodiment of the present invention, the magnetic nanoparticles take the form of a metal core coated in a material such as carbon as shown in FIG. 1B. These nanoparticles are then functionalized so that a bio-molecule can be bonded to them.

In one embodiment of the present invention, the magnetic nanoparticles are carbon nanotubes, such as single-walled carbon nanotubes (SWNT) embedded with magnetic metal atoms (FIG. 1A). In one embodiment, the magnetic metal atoms comprise nickel, iron or cobalt.

Single-walled carbon nanotubes are well known in the art and may be synthesized using any suitable technique, such as chemical vapor deposition technique (CVD). These carbon nanotubes are grown from a surface using nickel or yttrium, or both nickel and yttrium, as seed. In one embodiment, the nickel and/or yttrium is thus incorporated at least into the tip of the carbon nanotube. In one embodiment, suitable SWNTs have a diameter between about 1.2 to about 1.5 nm, and a length of about 2 to about 5 µm. The SWNTs may be either armchair or chiral nanotubes. In one embodiment, the SWNTs used are armchair (5,5) nanotubes.

The magnetic nanoparticles or carbon nanotubes are prepared for bonding to a bio-molecule by adding functional groups to them. These functional groups act as the bonding site, which will hold the bio-molecule to the nanoparticles or the carbon nanotubes. In addition, functionalization is important as many nanoparticles or carbon nanotubes, particularly SWNTs, are insoluble in water. Functionalization increases their water solubility.

Figure 4A:
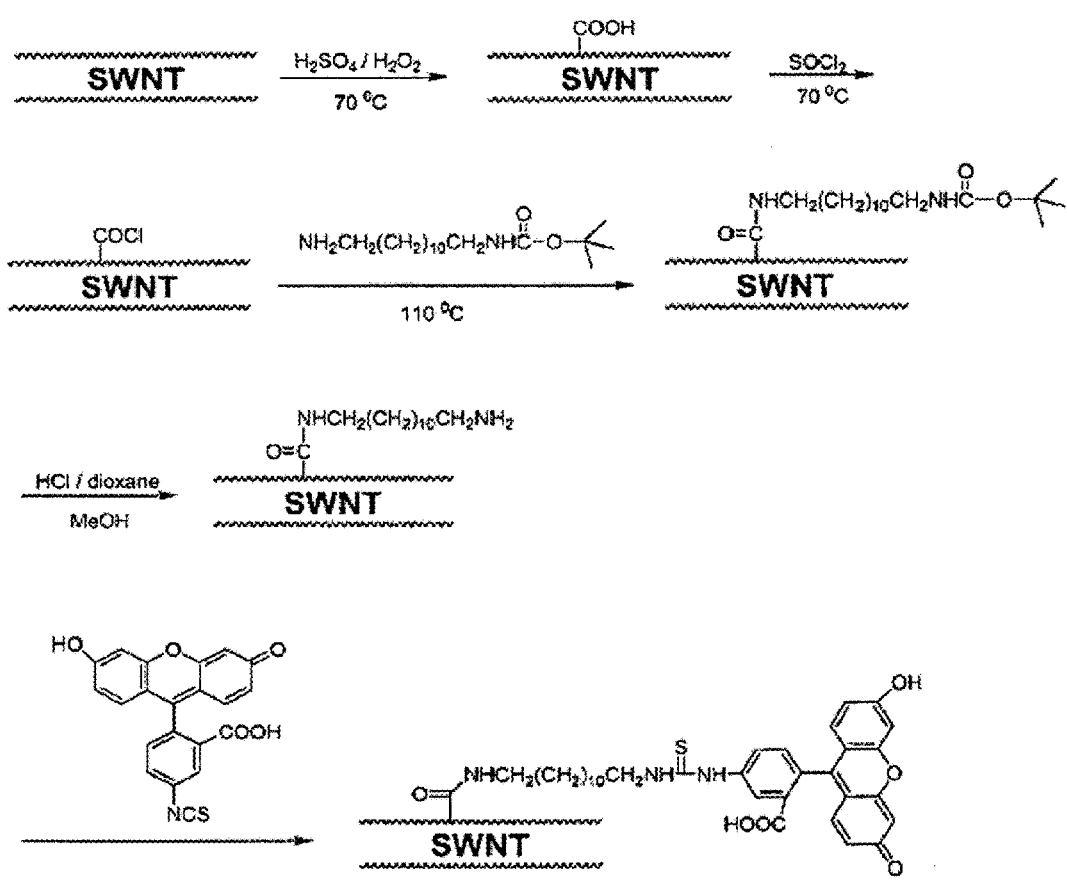
FIGS. 4A, 4B, 4C, and 4D show schematic processes for functionalizing a single-walled nanotube.
Figure 4B:
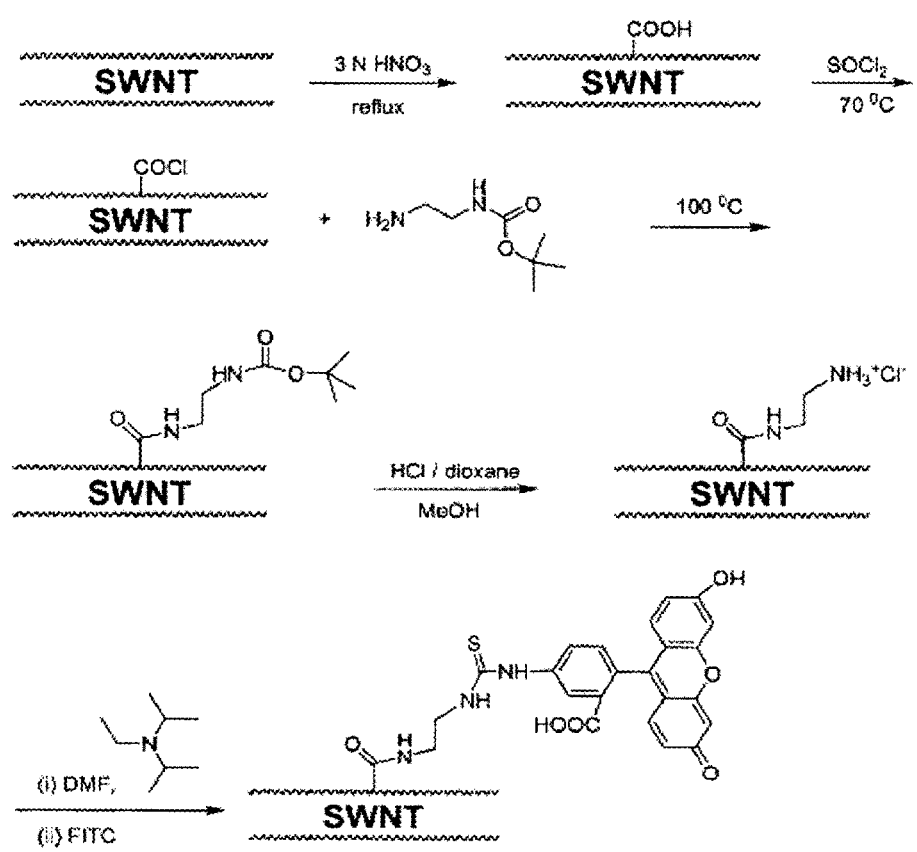

In one embodiment, shown schematically in FIGS. 4A and 4B, functionalization is achieved by chemically altering the surface of the carbon nanotube. In one example, the surface of the magnetic carbon nanotube is carboxylated and the carboxylic acid is reacted with thionyl chloride to provide an acid chloride. The acid chloride may then be coupled with tert-butyl-12-aminododecylcarbamate, or Pert-butyl(2-aminoethyl) carbamate, followed by deprotection of the Boc group to provide the amine derivative.

Figure 4C:
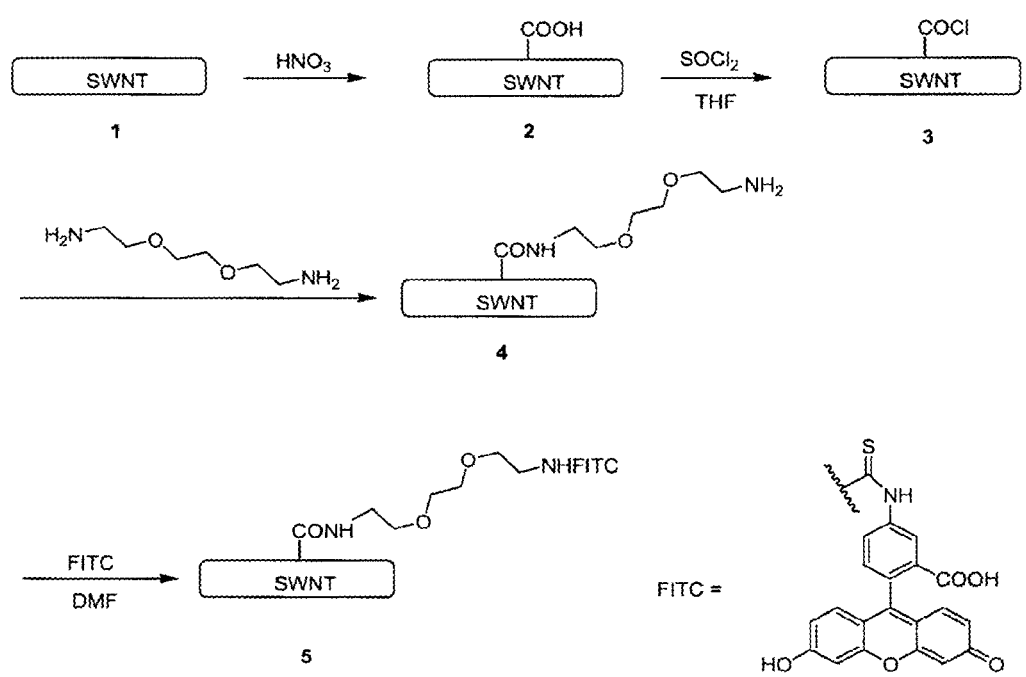
Figure 4D:
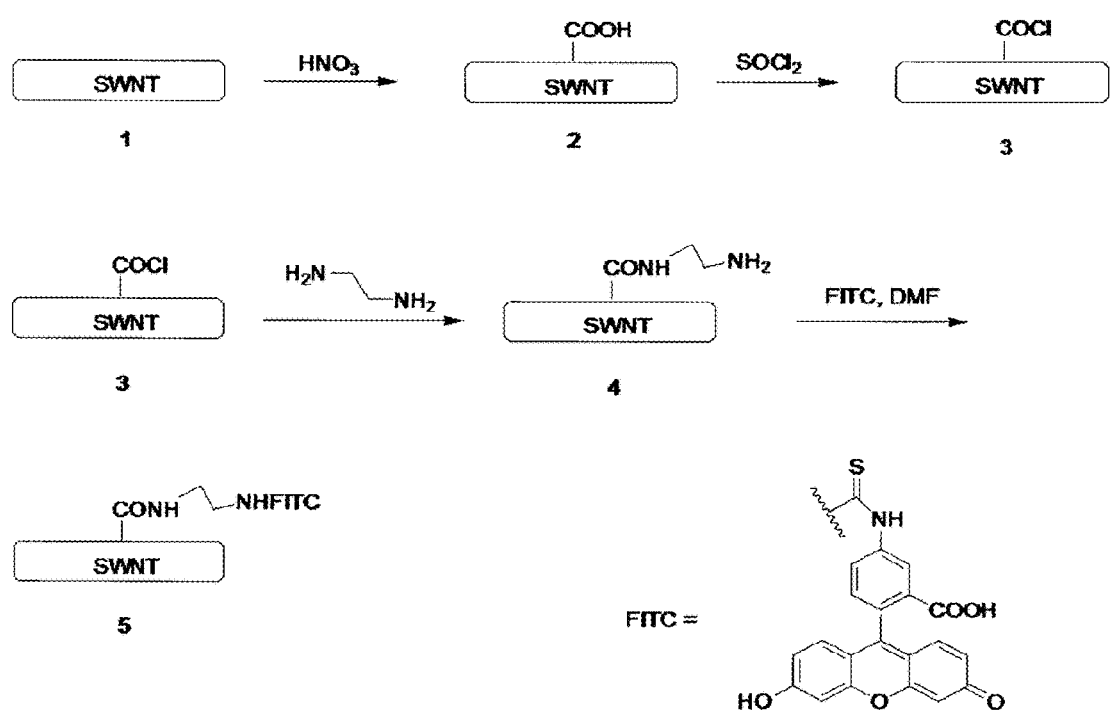

In an alternative embodiment, amine derivative nanotubes can be produced by reacting the acid chloride nanotube with then 2'-(ethylenedioxy)bis(ethylamine) to produce the amine derivative, as shown in FIG. 4C. In a further alternative, the amine derivative may be formed using ethane-1,2 diamine, as shown in FIG. 4D.

In one example, the amine derivative is then reacted with fluorescein isothiocyanate (FITC) giving rise to the FITC derivatized magnetic carbon nanotube.

These magnetic carbon nanotube bonded molecules may then be subjected to a magnetic field and a cell culture, as described herein.

Biomolecules such as DNA or RNA can be attached to carboxyl functional groups on the surface of the nanoparticle or carbon nanotube. In one example, plasmid vectors may be combined with carboxylated SWNTs and 1-ethyl-3-(3-dimethylaminopropyl) carbodiimide (EDC) in 2-[N-morpholino]ethane sulfonic acid (MES) or a phosphate buffer (pH 4.5) for the aminization between the primary amine groups in the DNA molecules and carboxylic groups on the nanotubes. Alternatively, DNA or RNA can be bound by electrostatic interaction with amine functional groups on the surface of the nanoparticle.

The nanoparticles may comprise silica or other materials which may be biodegradable or biocompatible within a cell, such as, without limitation, nanocellulose, or nanocrystalline cellulose. The term "biodegradable" as used herein means that the substance may be broken down into innocuous products by the action of living things. The term "biocompatible" means that the substance does not have toxic or injurious effects on biological function of cells either in vitro or in vivo. In one embodiment, a carbon nanotube may be coated with silica and the carbon then removed or burnt out, leaving a silica nanotube based on the carbon template. The silica nanotube may then functionalized using methods similar to those described herein for carbon nanotube, and as are known to those skilled in the art.

Figure 2:
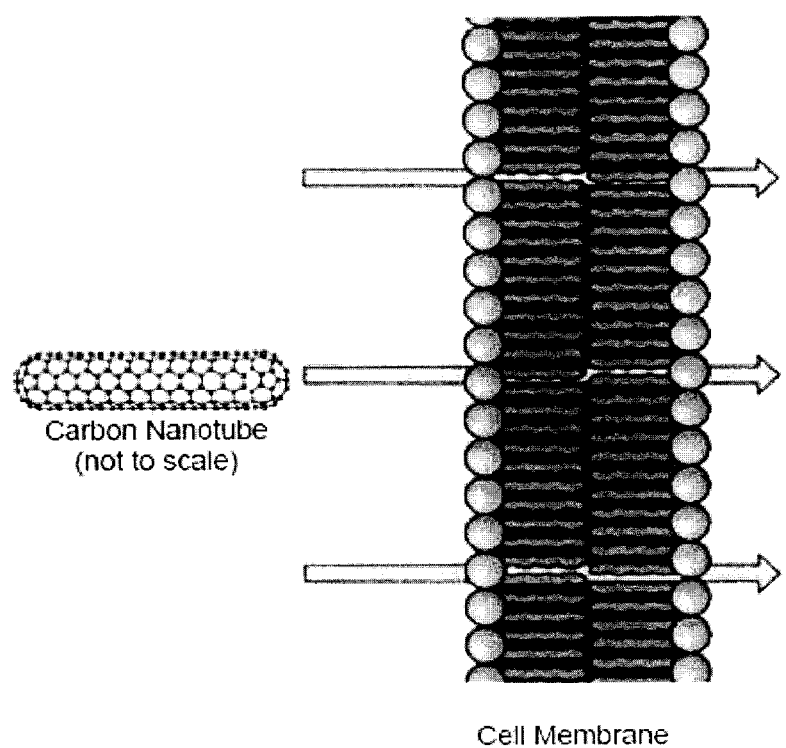
FIG. 2 shows the delivery vehicle being forced though the cell membrane. The arrows depict the magnetic field. In this depiction the carbon nanotube is being used for the delivery.

Once the biomolecule or other molecule of interest is bonded to the magnetic nanoparticle, the nanoparticle is placed in a solution along with the cells that are to be transfected and a magnetic force is applied so that the nanoparticles are accelerated through the solution. Inevitably, these will collide with a cell and there will be a probability that the particle will pass through the membrane into the cell, as shown schematically in FIG. 2. If the particle does not enter the cell, it will be free to accelerate again to attempt to transfect another cell. A substantial majority of the cells will be transfected after a relatively short period.

The magnetic field that is used to drive the molecular delivery vehicles is configured so that it provides a magnetic force which can be static or variable in direction and magnitude. In one embodiment, the magnetic field is configured so that the magnetic force can change between being variable and static at different stages of delivery. In one embodiment, the magnetic nanoparticles can be caused to move in complex paths by constantly varying magnetic force, which is changing its magnitude and direction.

In another embodiment, the delivery vehicles can be moved in complex paths and at variable velocities and accelerations.

In one embodiment, the membrane that must be transfected can be made more permeable by applying ultrasound energy to the cell culture, such as low-intensity pulsed ultrasound. The ultrasound may be applied at higher frequencies than is known to enhance cell growth. Typically LIPUS has been used at frequencies less than about 1 MHz, however, in embodiments of the present invention, any frequency between 1 MHz to 2 MHz may be used, such as 1.5 MHz.

Ultrasound can be applied using conventional or slightly modified therapeutic ultrasound transducers. The intensity of the ultrasound energy may vary from 0.1 W/cm$^2$ to about 1.0 W/cm$^2$. In one embodiment, the intensity is between about 0.3 W/cm$^2$ to about 0.5 W/cm$^2$. Varying duty cycles and pulse repetitions may be used, such as a duty cycle between about 20% and 100% and a repetition frequency of 100 Hz. In general, higher intensities and longer duty cycles will increase movement across cell membranes, at the expense of cell viability. Total ultrasound energy, calculated as follows, should preferably not exceed a level where cell viability is substantially impaired.

Energy$(J)$=Intensity*Duty Cycle*Time

In one embodiment, total energy may optimally be 18000 mJ.

Suitable ultrasound contrast agents, such as Definity™ (Bristol-Myers Squibb) may be used to promote microcavitation in the vicinity of the cells.

Figure 3:
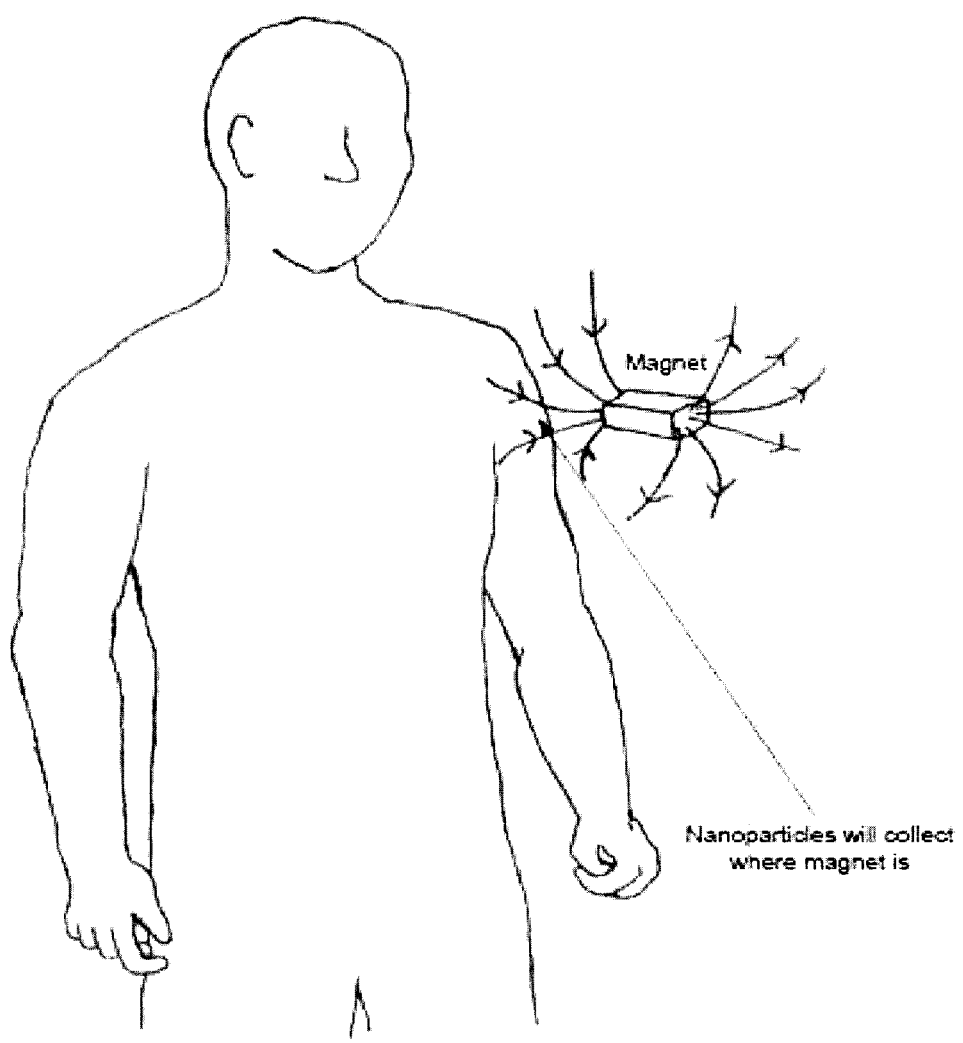
FIG. 3 depicts the use of a magnet to collect the nanoparticles at a certain location in the body. In this case the particles are being collected at the top of the patients left arm.

In one embodiment, the magnetic nanoparticles may be used in vivo to deliver therapeutic agents such as drugs or biomolecules to a specific target. A magnet may be placed at the site where the magnetic nanoparticles are to be focused, as shown in FIG. 3. As the magnetic nanoparticles circulate through the body, they will accumulate at the site where the magnet is located. Thus, the nanoparticles deliver the biomolecules to a specific target region.

In one embodiment, this targeted delivery mechanism may be used to deliver molecules into difficult to access areas, such as across the blood-brain barrier into the central nervous system. The magnetic nanoparticles can be collected at a specific site of the blood brain barrier using a magnetic field. Then, using a magnetic force these nanoparticles can be forced across the barrier.

Once the nanoparticles have been concentrated at a specific point or region, the nanoparticles can be forced into cells at that site by using a magnetic force with rapidly alternating direction. This will excite the particles to move back and forth quickly. As they move around they will collide with the cell membrane and at least a portion of the particles will pass through the membrane into the cell. In one embodiment, the use of ultrasound and magnetic forces may be used to enhance such movement in vivo. Ultrasound transducers which apply ultrasound energy to the human body are well known for imaging purposes, and may be used for the molecular delivery systems described herein with little or no modification.

The present invention may be embodied in other specific forms without departing from its structures, methods, or other essential characteristics as broadly described herein and claimed hereafter. The described embodiments are to be considered in all respects only as is, therefore, indicated by the appended claims, rather than by the foregoing description. All changes that come within the meaning and equivalence of the claims are to be embraced within their scope.

EXAMPLES

The following examples are intended to be illustrative of the described invention, and not be limiting of the invention claimed herein, except where specifically recited.

Example 1—Synthesis of FITC-Labelled Carbon Single-Walled Nanotubes (SWNT) (Scheme Shown in FIG. 4B)

Nickel containing carbon nanotubes were refluxed with 3N HNO$_3$ for 45 h to introduce carboxylic acid groups. After refluxing, the solution was diluted with deionized water, filtrated and washed several times with deionized water. The acid treated SWNTs were collected and dried under vacuum.

100 mg of SWNTs were stirred in 20 mL of SOCl$_2$ (containing 1 mL of dimethylformamide) at 70° C. for 24 h. After centrifugation, the brown-colored supernatant was decanted and the remaining solid was washed with anhydrous tetrahydrofuran. After centrifugation, the pale-colored supernatant was decanted. The remaining solid was dried under vacuum.

A mixture of the resulting SWNTs and 1 g of tert-butyl-2-aminoethylcarbamate was heated at 100° C. under an argon atmosphere for 100 h. After cooling to room temperature, the excess tert-butyl-2-aminoethylcarbamate was removed by washing with methanol. The resulting black solid was dried under vacuum.

The coupling product of SWNTs with tert-butyl-2-aminoethylcarbamate was suspended in MeOH and a solution of HCl in dioxane (4 N) added, the resulting mixture was stirred at room temperature for 4 h. Then anhydrous ethyl ether was added, the resulting precipitate was collected and dried under vacuum.

The amine groups-containing SWNTs were suspended in a mixture of DMF and diisopropylethylamine and a solution of fluoroisothiocyanate (FITC) in DMF was added. The resulting mixture was stirred for 4 h at room temperature in darkness. Then anhydrous ethyl ether was added, the resulted precipitate was collected by centrifugation and washed thoroughly with ethyl ether and methanol, dried under vacuum to give FITC-labeled SWNTs.

In an alternative method, shown schematically in FIG. 4C, SWNTs from Aldrich were oxidized to form carboxylic acid groups on the surface. These nanotubes were reacted with thionyl chloride and then 2'-(ethylenedioxy)bis(ethylamine) to produce amine-terminated nanotubes. The amine was then reacted with FITC to attach FITC to SWNTs.

Example 2—IR, XPS and UV-Vis Characterization

Figure 5A:
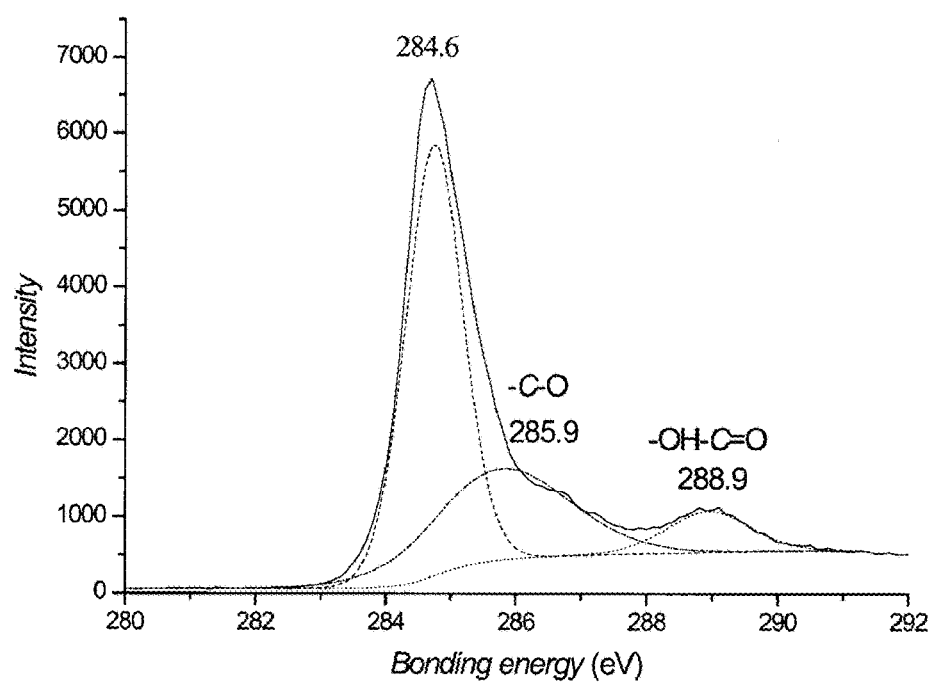
FIGS. 5A and 5B show XPS and IR spectra for carboxylated SWNTs.
Figure 5B:
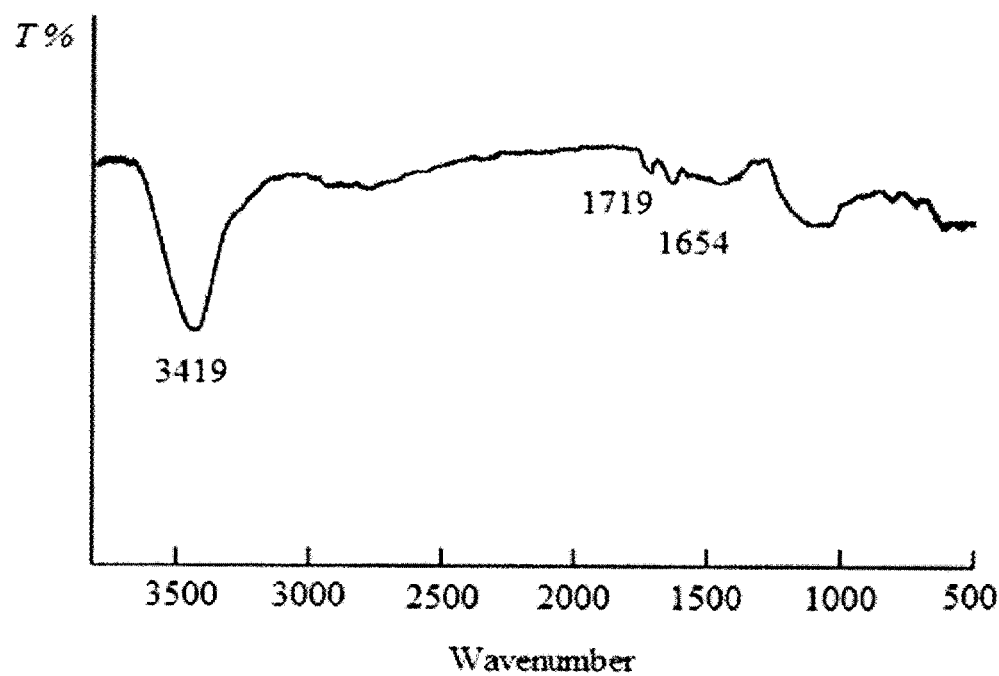
Figure 6A:
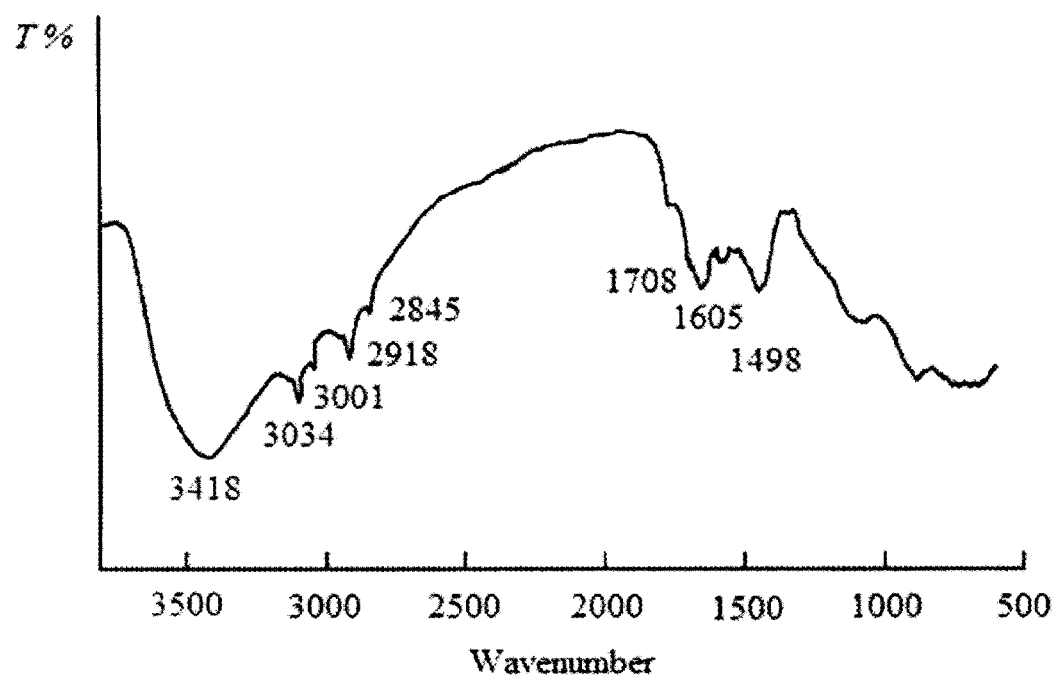
FIGS. 6A and 6B show IR and UV-vis spectra for FITC labelled SWNT. The vertical axis A shows absorption.
Figure 6B:
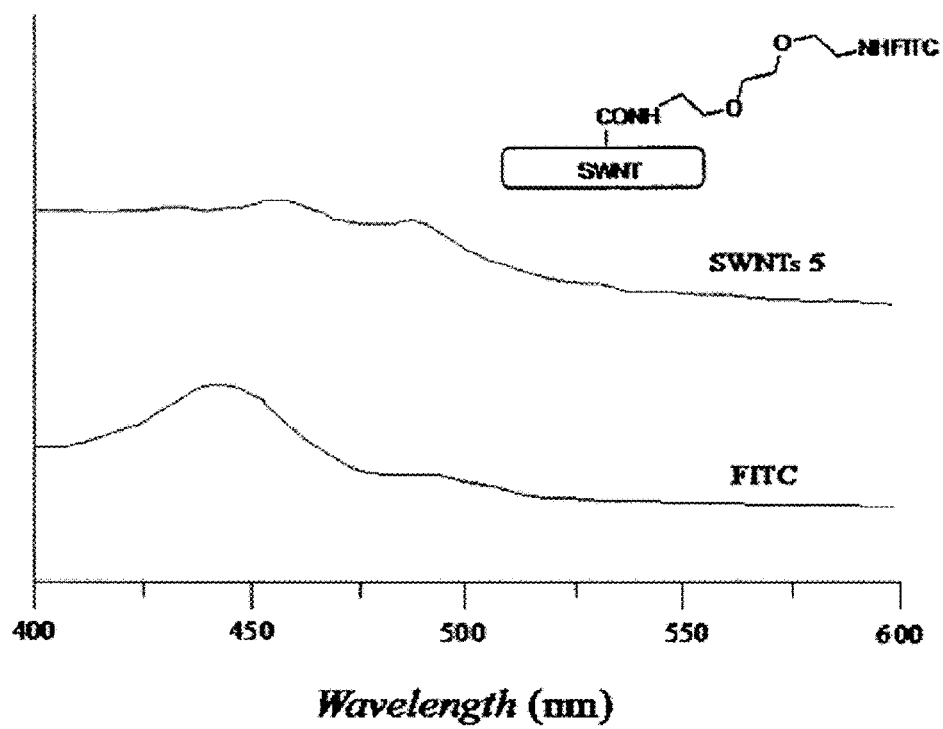
Figure 8A:
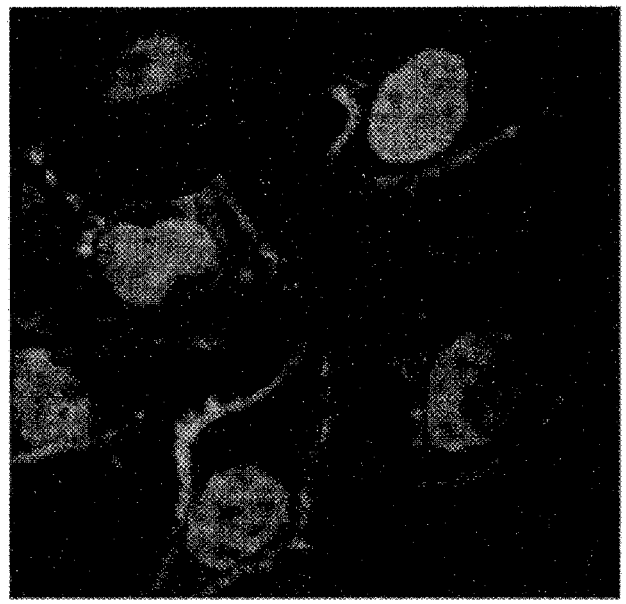
FIG. 8A show distribution of FITC labelled nanoparticles in control MCF-7 cells and FIG. 8B shows distribution in MCF-7 cells exposed FITC labelled magnetic nanoparticles and a magnetic field.

To validate the all synthesis take place, all of the intermediates shown in FIG. 4C and final product (SWNT-FITC) were characterized by Infrared (IR), X-ray photoelectron spectroscopy (XPS) and UV-vis and the results are shown in FIGS. 5 and 6. IR data clearly show that SWNTs were successfully functionalized to give carboxylic groups and XPS data show that about 6.1% of the carbon atoms are present as carboxyl groups. The UV-vis spectrum of the FITC-labeled SWNT in water is shown in FIG. 8, for comparison, the UV-vis spectrum of the FITC in water is shown in the same figure.

Example 3—Fluorescent Staining and Imaging

FITC-labeled SWNTs (CNT-FITC) as prepared using the method described in Example 1 (FIG. 4B) were used to stain and image a human breast adenocarcinoma cell.
Materials
Cell—MCF-7
Medium—GIBCO 11330, DMEM/F12 (1:1)
Formaldehyde Solution (w/v) 16%, Methanol-free, Pierce, Cat#28906
Hoechst—Invitrogen Cat#33342
Rhodamine Phalloidin—Invitrogen Cat# R-415
(Rhodamine Phalloidin 300U was dissolved in 1.5 ml Methanol to form concentration of 200 units/ml, distributed them into 10 μl each vial, store at −20° C.)
PBS buffer
Block buffer—PBS/0.5% BSA
Magnets—Applied Magnets Cat#ND075 (www.magnet4less.com) 2×1 in thick disc, Grade N42, Rare earth Neodymium super strong magnet (Pull force: 176 lbs)

Round cover slips were placed into a 6-well or 24-well plate, one cover slip into one well and MCF-7 cells into each well, cell number: $1 \times 10^5$/ml, and incubated at 37° C. over night. Add Hoechst into each well (1 μl Hoechst in 1 ml medium) and incubate at 37° C. for 1 h. 1 ml of CNT-FITC was added into each well of the plate (except the control) and incubate at 37° C. for 1 h. Each well was washed 3 times with PBS.

A cover slip picked out of one well with tweezers, and vertically inserted into a beaker containing 10 ml serum-free medium supplemented with CNT-FITC (10:1, medium: CNT-FITC) was placed on hotplate (magnetic stirrer) with the cells facing the incoming nanotubes for 3 min. The speed of the stirrer was set at 1,200 rpm. The cover slip was laid on one dish containing serum-free medium without CNT-FITC, and the dish was placed on a magnet for 7 min. The cover slip was then washed 3 times with PBS and placed in another 24 well plate, along with cover slips which were not placed on a magnet.

The cells were fixed with 4% Formaldehyde Solution for 10 min (or over night at 4° C.). The formaldehyde solution was removed and the cells washed 3 times with PBS. 250 ul of PBS/0.2 TX-100 was added onto the cover slips in the wells and place at room temperature for 10 min. Again the cells were washed 3 times with PBS, and blocked with 250 μl of PBS/0.5% BSA for 20 min. 2.5 μl Rhodamine Phalloidin was added to 50 μl block buffer and the mix pipetted on parafilm. The cover slip was overlaid onto the solution in place for 30 min.

The cover slips were then placed back to the plate and washed 3 times with PBS. The coverslips were then mounted onto slides and send for the confocal microscopy. Samples were imaged with a laser scanning confocal microscopy 510 (Carl Zeiss) equipped with Axiovert 100M microscopy (Zeiss), a F-Fluar 40X-1.3 NA oil lens and 3 different lasers (Uv, Argon/2 and HeNe1).

Figure 7A:
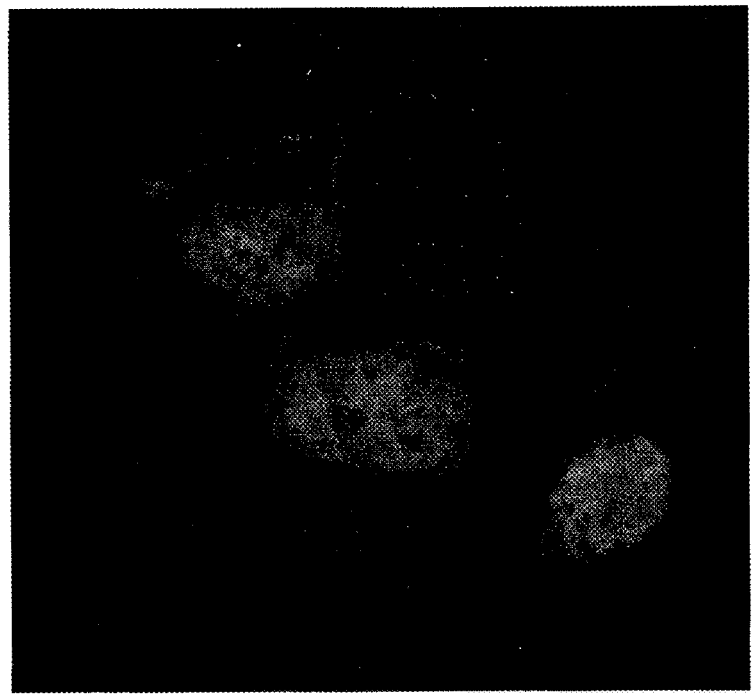
FIG. 7A shows a confocal microscopy image showing control cells.
Figure 7B:
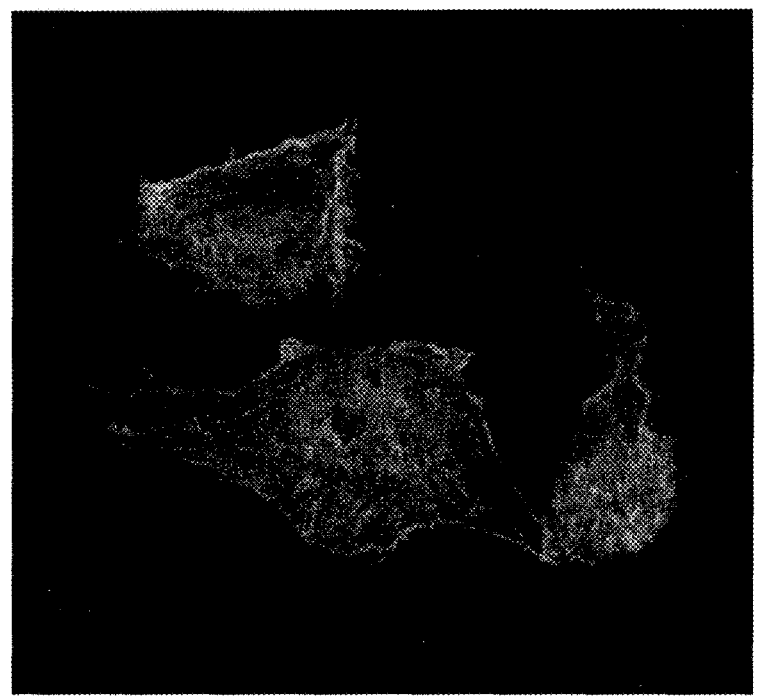
FIG. 7B shows cells a confocal microscopy image showing cells with FITC labelled nanoparticles in the cytoplasm.
Figure 7C:
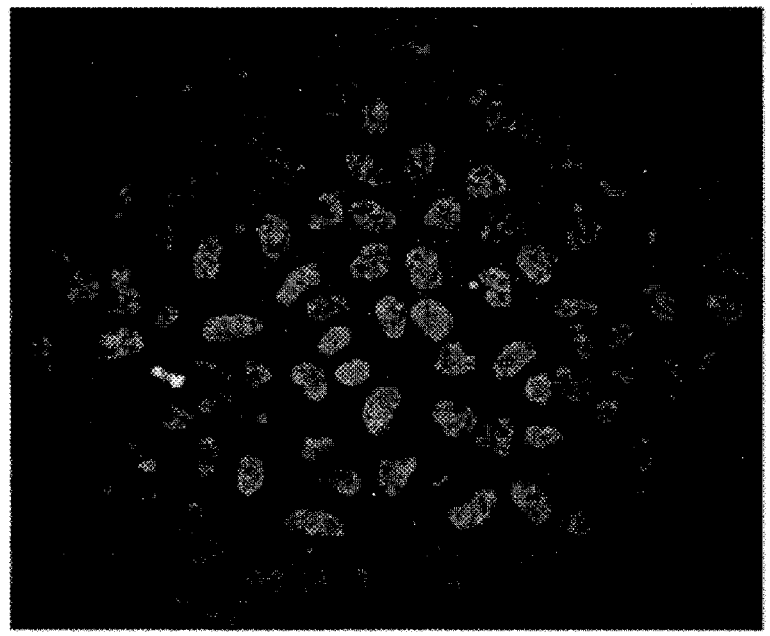
FIGS. 7C and 7D show confocal microscopy of MCF-7 control cells and cells transfected with nanoparticles bound with GFP plasmid.
Figure 7D:
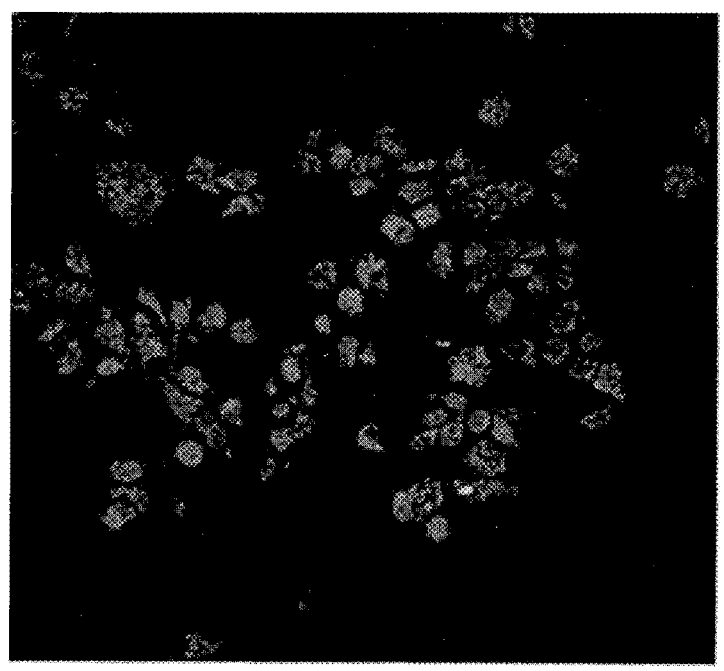
Figure 8B:
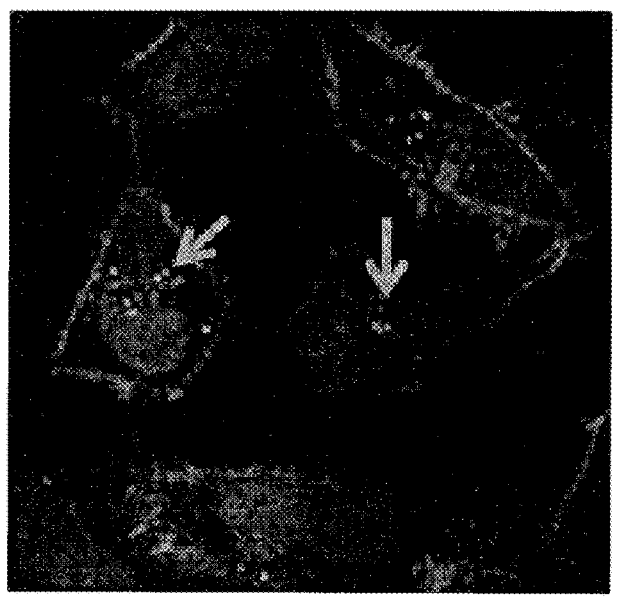

As shown in FIGS. 7 A and 7B, the cell nuclei fluoresce strongly as a result of the Invitrogen stain which combines with double-stranded DNA. In FIG. 8B, fluorescence of the FITC moieties may be plainly seen within the cells cytoplasm, indicating that the CNT-FITCs have passed through the cell membranes and into the cytoplasm.

In another example, SWNT were conjugated to GFP plasmid (pDRIVE5-GFP) by covalent bonding using EDC and a phosphate buffer. The SWNT-GFP plasmid was then incubated with MCF-7 cells for 3 min, followed by 7 minutes with a magnetic field supplied by a magnetic stirrer. The cells were then incubated for 24 hours and confocal microscopy was used to confirm GFP expression. FIG. 7D shows results of GFP fluorescence within the cells, as compared to the control cells in FIG. 7C.

Example 4—Cell Uptake Efficiency

Figure 9:
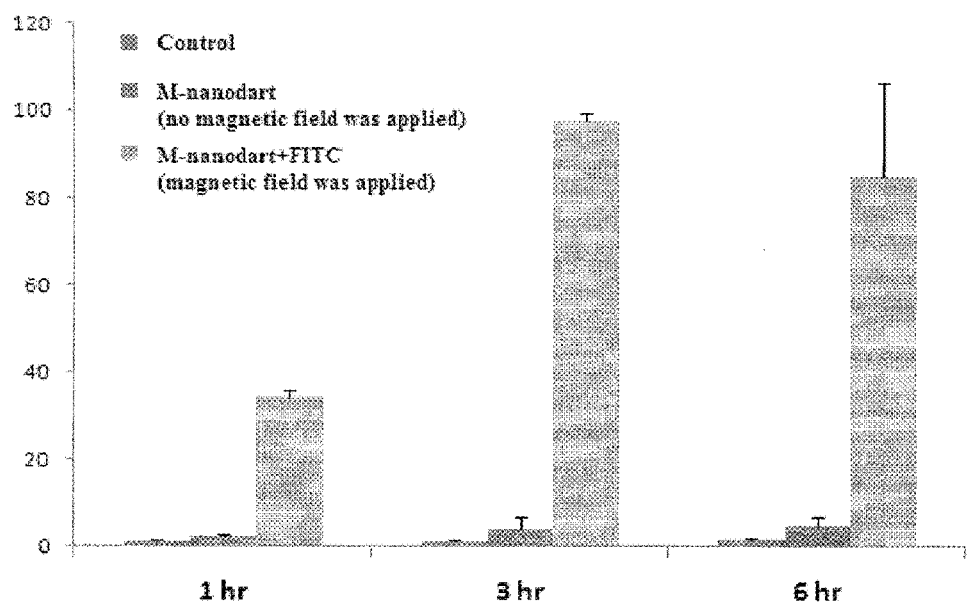
FIG. 9 shows a graph of percentage uptake by MCF-7 cells.

FITC-labeled SWNT was delivered into adherent MCF-7 breast cancer cells. Following the delivery and recovery phases, the fluorescently-labelled SWNT was detected by confocal microscopy. The results are presented in FIGS. 8 A and 8B. The data clearly shows that the SWNT crossed the cell membrane and entered the cell cytoplasm and even into the nucleus (refer to the green dots in FIG. 8B; some of them are pointed by the arrows). The uptake rate is about 90% shown in FIG. 9.

Figure 10:
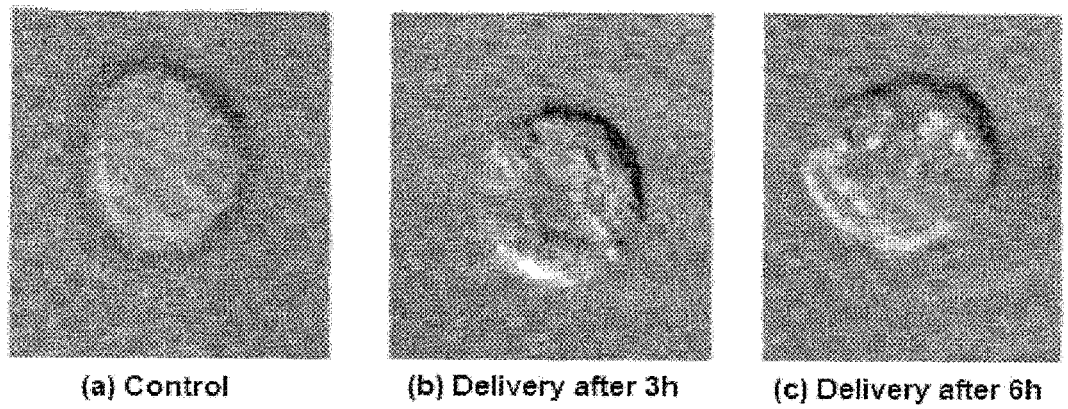
FIGS. 10(a), 10(b) and 10(c) show FITC labelled nanoparticles delivered into hematopoietic stem cells in a control, after 3 hours and after 6 hours, respectively.

In addition to delivery of FITC to adherent cells, like MCF-7 cells, we also successfully delivered FITC into difficult-to-transfect cells, or suspension cells, like hematopoietic stem cells (HSCs). FIG. 10 shows the delivery results. The results show that SWNT can deliver FITC into HSCs. As time increases to 3 and 6 hours, more FITC enters the cell (FITC shows as green fluorescence). The control sample showed no internal fluorescence.

Example 5—Cell Viability

Figure 11:
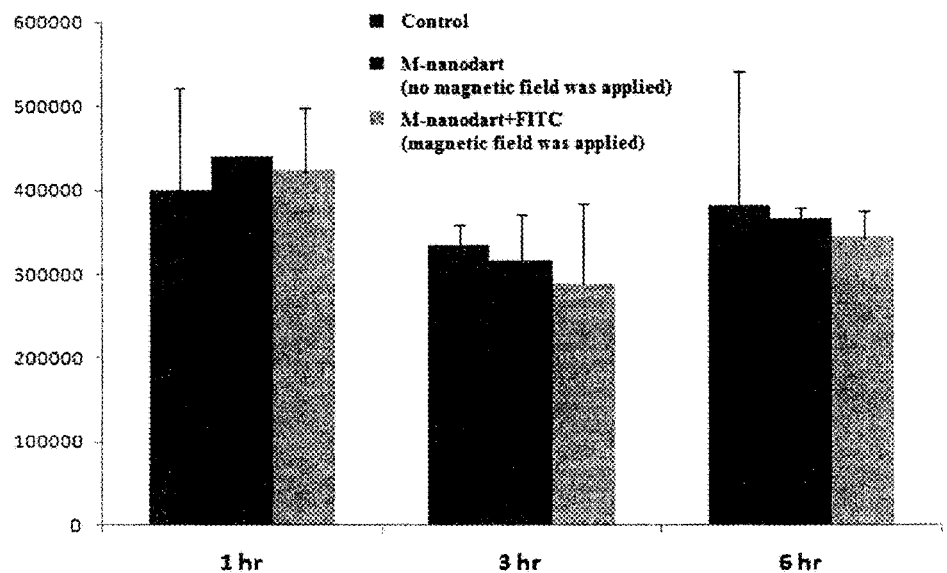
FIG. 11 shows a graph demonstrating viability of MCF-7 cells after FITC labelled nanoparticle uptake compared to control cells.
Figure 12A:
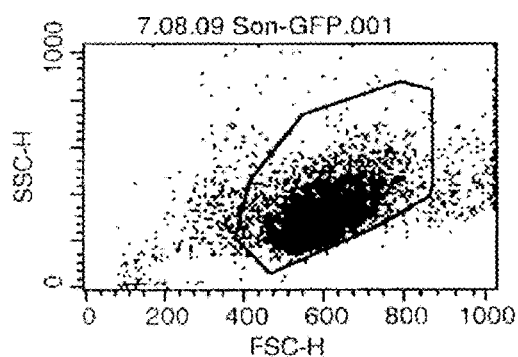
FIG. 12A shows FACS results for Negative control sample contained no GFP plasmid, no Definity, and was not sonicated. FACs results: Marker: MI, % Gated: 0.16. Extremely high cell viability is observed.
Figure 12B:
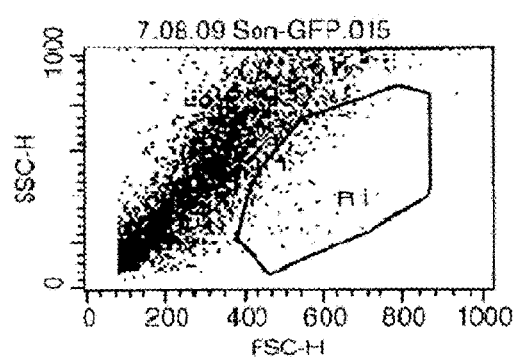
FIG. 12B shows FACS results for Positive control sample contained 2 µg of GFP plasmid, no Definity, the lipofection agent PEI, and was not sonicated. FACs results: Marker: MI, % Gated: 33.12%. Very low cell viability is observed.
Figure 13:
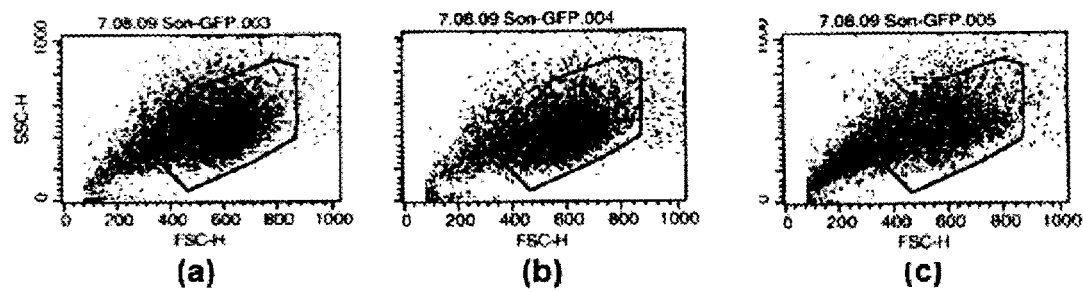
FIG. 13 shows FACS results FACs results for sample sonicated at 0.5 W/cm2, with a 20% duty cycle for 60 seconds. DNA plasmid concentration was varied.
Figure 14:
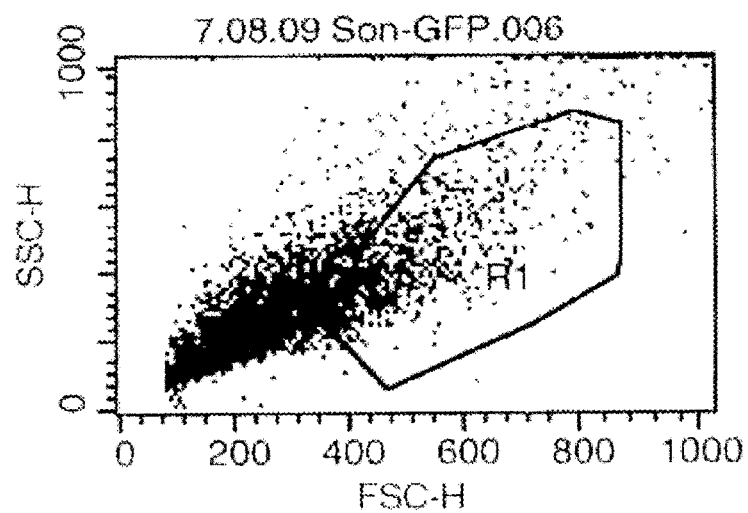
FIG. 14 shows FACs result for sample sonicated at 0.3 W/cm$^2$, with a 100% duty cycle for 60 seconds. DNA plasmid concentration was 30 µg/mL. FACs results: marker: MI, % Gated: 14.67. Cell viability is observed to have decreased.
Figure 15:
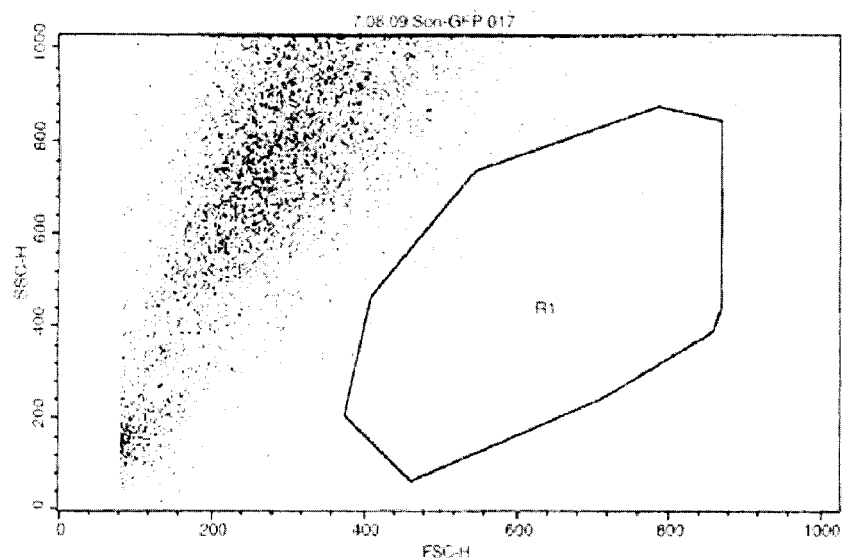
FIG. 15 FACs result for sample sonicated at 0.5 W/cm$^2$, with a 100% duty cycle for 60 seconds. DNA plasmid concentration was 30 µg/mL. FACs results: marker: MI, % Gated: 32.12. Cell viability is observed to be low.

Furthermore, it is worth noting that cell viability was not compromised by SWNT uptake when compared with control, as shown in FIG. 11. Viability of MCF-7 cells after FITC-SWNT uptake with exposure to a magnetic field was compared to the control cells and cells exposed to SWNT alone with no magnetic field. Cells exposed to SWNT appear to substantially similar to control populations for viability after 6 hours.

Example 6—Ultrasound Delivery (USD)—Cell Preparation and DNA

USD and transfection was assessed using human breast adenocarcinoma cells (MCF-7). Cells were maintained in the IMDM medium with 10% fetal bovine serum. Cells were harvested a day before the experiment by adding 0.25% Trypsin to the culturing flask and waiting for detachment. 1 mL of cells was added to 10 mm×35 mm dishes with an additional 1 mL of medium. Cell concentration was approximately $1.5 \times 10^5$ cells/mL. To determine transfection, green fluorescence protein plasmid (GFP plasmid-pDRIVE5-GFP) was added to the medium 15 minutes before sonication. Various concentrations of GFP were used: 2 µg/mL, 15 µg/mL, and 30 µg/mL. The ultrasound contrast agent Definity, purchased from Lantheus Medical, was used to promote cavitation. The UCA volume used was 140 µL.

USD was performed using the Excel UltraMax therapeutic ultrasound machine, probe radius 2.5 cm. The ultrasound probe was coupled to the bottom of the cell dish using ultrasound gel. Ultrasound was applied for 60 seconds, at a 1 MHz frequency with varying output intensity: 0.3 W/cm$^2$, and 0.5 W/cm$^2$. The duty cycle was tested at 100% or 20% with a fixed pulse-repetition frequency of 100 Hz. As controls, we sonicated blank samples with no UCAs or GFP, and samples with GFP but no UCAs. Additionally, we ran a positive control using PEI, a lipofection agent. Finally, we prepared a sample that was not stimulated by ultrasound, but contained both Definity and GFP.

Cell counting was conducted in a fluorescence-activated cell-sorting (FACS) machine. 24 hours after USD, cells were collected in FACS test tube with 0.25% trypsin and washed once with 1×PBS. After all above, cells were resuspended in 200 uL 1% paraformaldehyde and tested through flow cytometry.

Cell viability was assessed by a cell count using a hemacytometer. After collecting cells in the FACS test tube, transfer 20 µl of each sample into small centrifuge tubes and dilute with 0.4% trypan blue. Put 10 µl in the hemacytometer and count cell number. Finally calculate the cell concentration with the following formula: Cell number counted in all squares/total number of squares counted*dilution factor*1× 10$^4$.

All the FACs test results are shown in FIGS. 12 to 15. Our negative control samples did not yield any transfection, but maintained excellent cell viability, as seen in the FACs result. The PEI lipofection positive control showed GFP expression, and extreme cell death.

TABLE 1

Transfection results of positive and negative control

|   | GFP [µg] | Definity [µL] | W/cm$^2$-DC-sec | % Transfection |
|---|---|---|---|---|
| 1. | 0 | 0 | 0-0-0 | 0.16% |
| 2. | 2 | 0 | 0-0-0 | 0.29% |
| 3. | 2 + PEI | 0 | 0-0-0 | 33.12% |

FACs analysis shows that as the exposure intensity increased the cell viability decreased. The maximum transfection was seen with an output intensity of 0.5 W/cm$^2$ and a 20% duty cycle, at 32.51%. Cell viability is significantly lower at the output intensities above this level. This result suggests that the output energy achieved by a 0.5 W/cm$^2$ and a 20% duty cycle, for 60 seconds is optimum for effective transfection.

The effect of DNA concentration on transfection efficiency was examined at every energy level. In every case, increasing the DNA concentration leads to an increase in transfection.

TABLE 2

Transfection results for varied ultrasound output intensity, and GFP concentration.

| GFP [µg] | Definity [µL] | Output intensity, Duty cycle | Transfection % |
|---|---|---|---|
| 2 | 140 | 0.5 W/cm$^2$, 20% | 16.20% |
| 15 | 140 | 0.5 W/cm$^2$, 20% | 26.93% |
| 30 | 140 | 0.5 W/cm$^2$, 20% | 32.51% |
| 2 | 140 | 0.3 W/cm$^2$, 100% | 7.52% |
| 15 | 140 | 0.3 W/cm$^2$, 100% | 9.71% |
| 30 | 140 | 0.3 W/cm$^2$, 100% | 14.67% |
| 2 | 140 | 0.5 W/cm$^2$, 100% | 19.63% |
| 15 | 140 | 0.5 W/cm$^2$, 100% | 26.76% |
| 30 | 140 | 0.5 W/cm$^2$, 100% | 32.12% |

MCF-7 cells were used to evaluate the effects of ultrasound on gene delivery. We found that the efficiency of ultrasound mediated gene delivery, depended on plasmid concentration, while the viability of the cells was directly related to the ultrasound's output intensity. The latter could be due to the fact that the other physical effects of ultrasound, such as transient increase of local temperatures and pressure, are detrimental to cells, or that the pores the cavitation effect opened were unable to re-seal.

The results from the negative control samples show that the DNA plasmid GFP is unable to diffuse across the cell membrane on its own. The USD results show that the application of ultrasound with UCAs allow the DNA plasmid to transfect and be expressed by the cell. Furthermore, our results demonstrate that there is an optimum ultrasound exposure level for transfection and cell viability; the existence of optimum exposure parameters is consisted with other literary results. The FACs results exhibit that any output energy greater than 18000 mJ is detrimental to cell viability, where:

Energy($J$)=Intensity*Duty Cycle*Time

Due to the nature of the FACs analysis, the transfection results obtained from the 0.5 W/cm$^2$, 100% duty cycle sample may be skewed. Since a high percentage of cells in this sample were dead, transfection percentage we obtained is misrepresented and cannot be compared to our results obtained with higher cell viability.

Plasmid concentration was an important factor in determining transfection efficiency. In every case, transfection rate increased with DNA concentration. This result leads us to consider the importance of DNA proximity to the cells during USD. However, it is expected that the effect of increasing plasmid concentration to increase transfection efficiency will eventually plateau.

The findings from the lipofection agent, PEI, revealed two results. First, it confirms that the plasmid GFP can be expressed by the MCF-7 cells, but more importantly it highlights the importance of USD. The FACs results show an extremely high amount of cell death due to PEI. In contrast, USD was able to obtain similar transfection efficiency while maintaining a much lower cell death rate.

Example 7—Formation of Silica Nanotubes

An amount of magnetic single-walled carbon nanotube powder was mixed with ground $Na_2SiO_3.9H_2O$ ($Na_2SiO_3.9H_2O$/carbon nanotube ratio was 0.2 by volume). The mixture was ground carefully for 10 min to mix the reactants uniformly. Excessively ground $NH_4Cl$ ($NH_4Cl$/$Na_2SiO_3.9H_2O$=3 by volume) was then added to the mixture. After being ground carefully for 50 min, the product was aged for 5 h and then washed three times with distilled water. Silicon dioxide coated nanotubes (Si-NT) were obtained after being dried at 60° C. for 5 h.

Particles core level spectra were measured using X-ray photoelectron spectrometer (VG ESCALAB MK II). The excitation source was a Mg X-ray anode and HV equalled to To determine crystallite sizes and phase purity of the powders, the X-ray diffraction spectrum was obtained with a Rigaku D/max-rA X-ray diffractometer using Cu Kα ($\lambda$=1.54056 A) radiation.

Figure 16:
FIG. 16 shows a picture of a biocompatible silica nanotube.

Si-NT' morphology was observed with JEOL JEM 2010 transmission electron microscope (TEM) operating at 200 kV, as shown in FIG. 16. TEM samples were prepared by dispersing a small amount of powder in ethanol. A drop of the dispersion was then transferred onto coated grid and died for observation.

Example 8—Si-NT Functionalization

Oxidation of the Si-NTs: The Si-NTs (200 mg) were refluxed to introduce carboxylic groups. After refluxing, the solution was diluted with deionized water, filtered over a 0.2 µm polycarbonate filter (Millipore) and washed several times with deionized water. The sample was collected and dried overnight in a vacuum oven at 800 C to give Si-NT-2 (170 mg).

Figure 17:
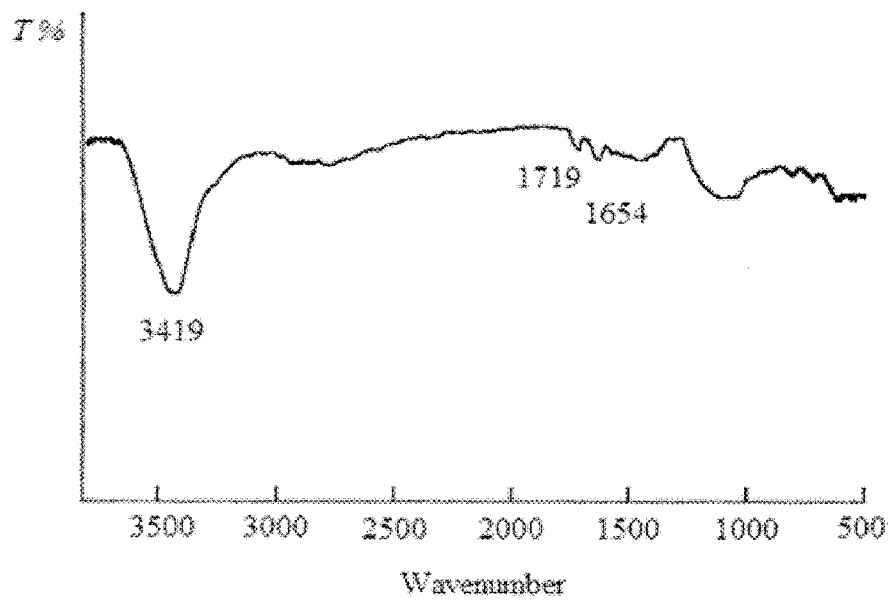
FIG. 17 shows a graph of IR spectra of Si-NT which has been carboxylated.

The carboxylated Si-NT underwent IR spectrum analysis, with the results shown in FIG. 17.

Reaction with thionyl chloride to give Si-NT-COCl: A suspension of Si-NT-2 (100 mg) in 20 mL of $SOCl_2$ together with 5 drops of dimethylformamide (DMF), was stirred at 70° C. for 24 h. The mixture was cooled and centrifuged at 2000 rpm for 30 min. The excess $SOCl_2$ was decanted and the resulting black solid was washed with anhydrous THF (3×20 mL), dried overnight in a vacuum oven at 80° C. to give Si-NT-3 (78 mg).

Coupling with ethylenediamine: The mixture of Si-NT-3 (50 mg) and anhydrous ethylenediamine (120 mL) was heated at 100° C. for 100 h. During this time, the liquid phase became dark. After cooling, the mixture was poured into methanol (100 mL), centrifuged to give a black solid, which was washed several times with methanol. The resulting solid was dried overnight in a vacuum oven at 80° C. to give Si-NT-4 (42 mg).

Functionalization with GFP plasmid: A suspension of the Si-NT-4 (25 mg) and GFP plasmid (5 mg) in anhydrous DMF (10 mL) was stirred in dark for 5 h, then the reaction mixture was poured into anhydrous ethyl ether (40 mL), centrifuged to give a black solid, which was washed with methanol until TLC (10% MeOH in dichloromethane) showed no free GFP left. The product was dried overnight in a vacuum oven at 80° C. to get the final product (23 mg), Si-NT-GFP.

Example 9—Transfection of HeLa

HeLa cells were grown in RPMI 1640 supplemented with 10% FB in 35 mm Petri dish with a cover slip.

Si-NT-GFP solution was prepared by weighing 3 mg Si-NT-GFP powder into 50 ml centrifuge tube. 3 ml of sterilized DI water was added and sonicated until the silica tube powder dissolve and incubated for 1 hr at room temperature. The final volume was brought to 50 ml using RPMI 1640 medium w/o FBS. A similar solution with Si-NT was prepared as a control. The test and control silica tube solutions were added to 100 ml beakers.

200,000 cells were seeded per dish and cultured overnight allowing cells to attach. A volume of test or controls solutions were added to the dishes and the cells were then magnetically treated for 3 min vertically by putting dishes on top of magnetic stir hot plate and followed by 7 mins with Petri dishes on top of a stirring magnet.

The cells were washed twice with PBS, and replaced with 2 ml of culture medium. The dishes were returned to incubator and incubated for 24 hr and 48 hr, respectively.

Figure 18:
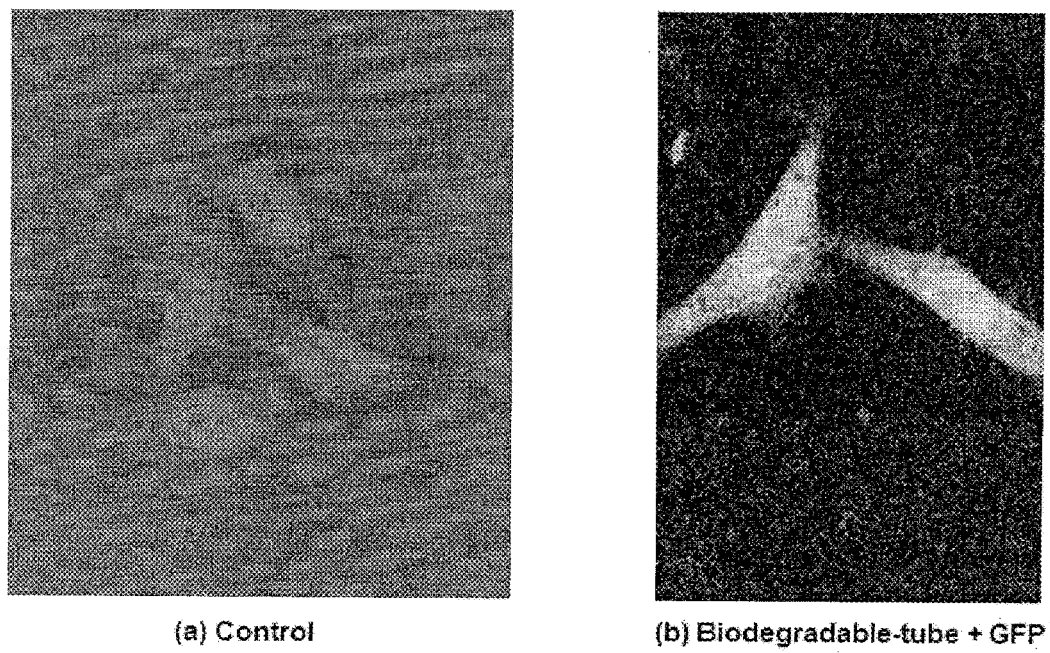
FIG. 18 shows HeLa cells which have been transfected with Si-NT-GFP plasmid, compared with a control.

Each of the samples were prepared for and viewed with confocal microscope observation of the GFP signal. The results are shown in FIG. 18.

Figure 19:
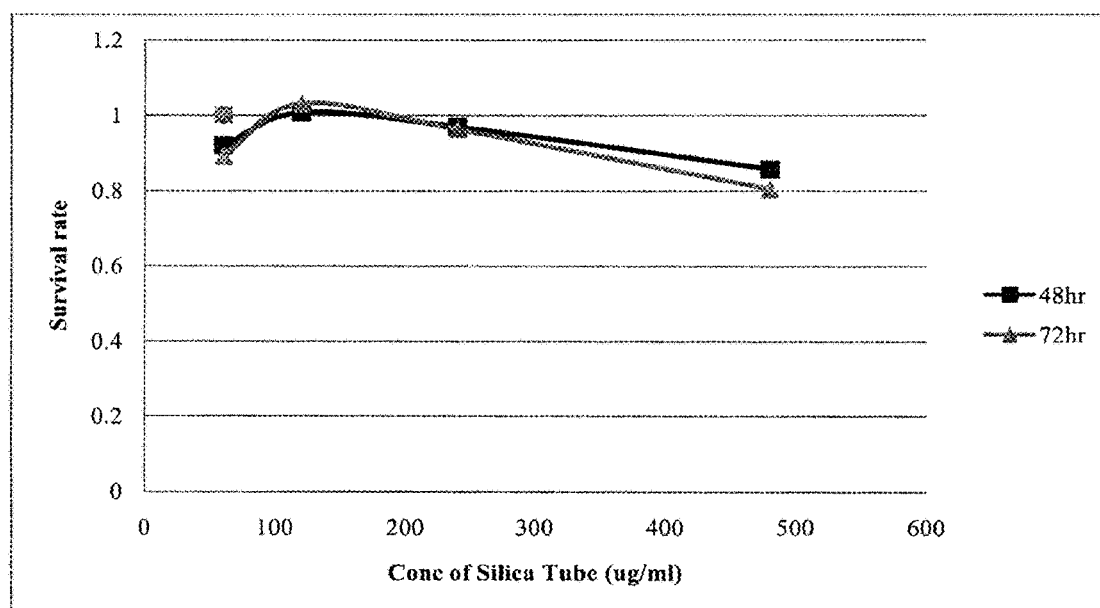
FIG. 19 shows a graph demonstrating low toxicity of the Si-NT after 48 and 72 hours of incubation.

Toxicity studies showed that increasing concentrations of Si-NT had little effect on cell survival rate, as shown in FIG. 19.

Example 10—FITC Delivery into Plant Cells Using Magnetic Single-Wall Carbon Nanotubes Experiments and Methods Cell Culture:

MD cell suspensions of canola (*B. napus* L. var. *Jet Neuf*) are maintained on a rotary shaker (160 rpm) at 20° C. in NLN media (pH 6.0, containing 6.5% sucrose, 30 mg $l^{-1}$ glutathione, 800 mg $l^{-1}$ glutamine, 100 mg $l^{-1}$ L-serine, 0.5 mg I-1 a-naphthaleneacetic acid (NAA), 0.05 mg $l^{-1}$ 6-benzylaminopurine (BA) and 0.5 mg $l^{-1}$ 2,4-D) (13). At 2-week intervals, one third of the mass of cells grown in 125 ml flasks is transferred to 50 ml of fresh NLN medium. Seeds of carrot (*D. carota* L. var. *Konservnaja* 63) are obtained from Plant Gene Resources of Canada (Saskatoon, Saskatchewan). Cells derived from leaves of in vitro plants are cultured in MS media, 3% sucrose, 0.2 mg $l^{-1}$ BA, 1.0 mg $l^{-1}$ NAA (pH=6). Two to Three days after subculture, cells are used for protoplast isolation.

Protoplast Isolation:

Plant cells are preplasmolyzed by incubation in CPW13M solution for 1 h at room temperature. The solution was then replaced with a digestion solution, consisting of ½ MS salts, 0.06% 2-(N-Morpholino)ethanesulfonic acid (MES), 13% mannitol, 0.1% Macerozyme R-10 (Yakult Honsha Co., Japan) and 0.5% Cellulase Onozuka R-10 (Yakult Honsha Co., Japan), pH 5.8. The incubation is carried out overnight (16 h) at 25° C. in the dark. The digestion mixture was filtered through a sterile nylon cell strainer (40 µm, BD Falcon, USA) to remove the debris, and then centrifuged (100×g) for 10 min. The pellet was resuspended in CPW25S and 2 ml of CPW13M was added to the top. The protoplasts are then collected with sterilized Pasteur pipettes following centrifugation (100×g) for 10 min, washed twice, and finally resuspended in ½ NLN medium supplemented with 13% mannitol. The protoplast solution was used for the mSW-CNT-FITC delivery experiment.

Synthesis of mSWCNT-FITC:

2 mg of purified mSWCNTs is dissolved into a 120 ml flask containing 5 ml of concentrated $H_2SO_4/HNO_3$ (V:V=3:1). The solution is sonicated for 10 minutes, and then washed completely. The mSWCNTs are resuspensed into a 120 ml flask containing 200 ml of MilliQ water. 5 mg of 1-ethyl-3-(3-dimethylaminopropyl) carbondiamide hydrochloride (EDC) and 1 ml of ethyl diamine are added into the flask. The mixture is stirred for 30 minutes in the dark. The solution is dialysed until no free ethyl diamine and EDC remained in solution. 100 mg of FITC is dissolved into 10 ml of DMF and added into the dialysed solution. The mixture is stirred for 5 minutes and kept at room temperature overnight. The mixture solution is dialysed until no free FITC molecules remained in solution.

Magnetic-Field-Driven Cellular Uptake Experiment:

Protoplasts with a density of $5 \times 10^5$ cells/plate are placed in 35 mm culture dishes and the dishes are sealed with parafilm. The magnetic-field-driven delivery method is carried out by placing the culture dishes containing 1 ml of medium with 0.25 µg/ml mSWCNT-FITC or mSWCNT on the top of an Nd—Fe—B permanent magnet for 12 h, then the protoplasts are collected, fixed in 2% paraformaldehyde and completely washed twice with PBS and 70% ethanol.

Cell Viability:

Protoplasts are seeded in 35 mm Petri dishes in culture medium. 30 µl of mSWCNTs is added into each dish. The Petri dishes are put on top of the Nd—Fe—B magnet at room temperature overnight. A drop of cell solution is deposited on a glass microscope slide and stained with FDA. Images are taken with both bright and green channels under a fluorescent microscope (Leica CW 225 A with Nikon digital camera DXM1200). The number of protoplasts is counted under bright channel and fluorescent channel. Then cell viability or NPs cytotoxicity is calculated.

Flow Cytometry Measurement:

Protoplasts exposed to mSWCNT-FITC at different concentrations are collected and centrifuged at 1000 rpm for 10 min. The collected cells are extensively washed using PBS, and then fixed in 2% paraformaldehyde. The fixed cells are washed with 70% ethanol twice again, and then resuspended in 400 µl PBS. The mSWCNT-FITC delivery efficiency is evaluated with Flow Cytometry (FACscan, Becton-Dickinson, San Jose, Calif., USA) at an excitation wavelength of 488 nm.

Atomic Force Microscope (AFM) Imaging:

A small amount of sample solution is directly transferred dropwise onto a silicon wafer. The sample is covered and kept at room temperature until the solution is dry. AFM images are taken using a Veeco Multimode V SPM operating in tapping mode.

Confocal Microscopy Imaging of Plant Cells:

Protoplasts are seeded at a density of $1 \times 10^5$ cells/cm² on cover slips previously coated with poly-L-lysine (10 µg/ml) for 45 min. The protoplasts are exposed to 0.25 µg/ml mSWCNT-FITC and mSWCNT alone (the control) on an Nd—Fe—B permanent magnet. After 12 hours of incubation on an Nd—Fe—B permanent magnet, the cells are fixed in 2% paraformaldehyde and washed twice with PBS buffer and twice with 70% ethanol. The sample is examined under a confocal laser scanning microscope (Quorum Wave FX-Sinning Disk) equipped with imaging software—Hamamatsu EMCCD (C9100-13).

TEM Imaging:

TEM images are taken using a Philips-FEI Morgagni 268 instrument operated at 80 kV. The sample solution is deposited on a copper support, which is coated with carbon. Protoplasts are fixed in 2% glutaraldehyde in 4% PEA/ cacodylate buffer, pH 7.2, for 2 hours at room temperature. (a) The fixative solution is drained off and replaced with 0.1 M PBS buffer. Two further changes are done 10 minutes apart. (b) The buffer is drained off and the sample is post-fixed with 1% osmium tetroxide ($OSO_4$ in 0.12 M Cacodylate buffer, pH 7.2) for one hour. (c) The sample is washed using 0.1 M phosphate buffer 3 times for a total of one half hour. (d) The sample is dehydrated through a graded ethanol series as follows: 50%, 70%, 90%, 100×3 changes; one change every 15 minutes. (e) The ethanol is drained off from the specimen and new ethanol: Spurr mix is added for 3 hours. The ethanol: Spurr mix is replaced with pure Spurr resin. The Petri dish is sealed overnight. (f) The Spurr resin is replaced again and the sample is dried at 70-80° C. in an oven for 18 hours. (g) The sample is cooled and then removed from molds. (h) The sample is ultracut by a Reichert-Jung Ultramicrotome and stained with uranyl acetate and lead citrate.

Synthesis of mSWCNT-FITC

Figure 20:
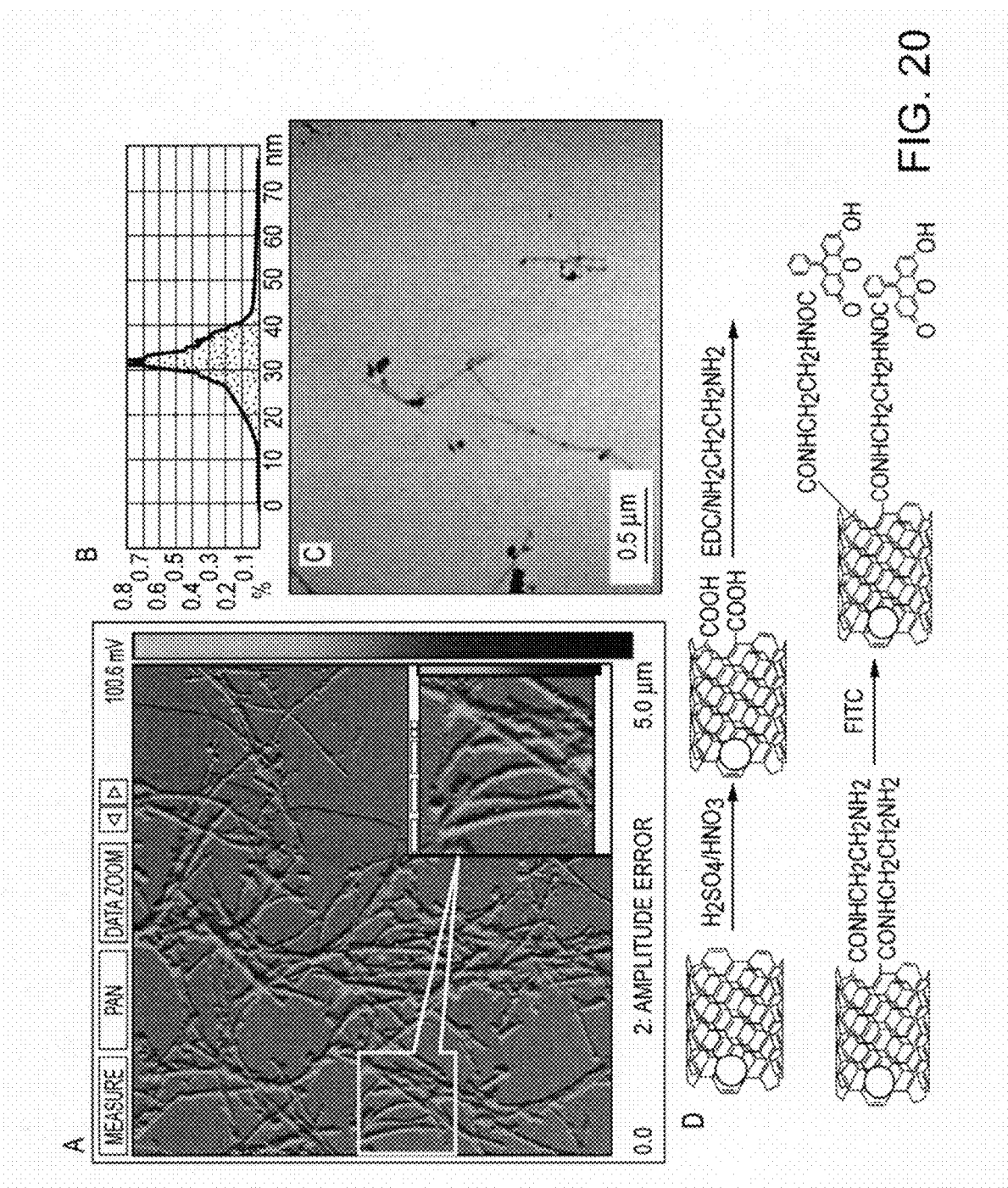
FIG. 20 shows the mSWCNT characteristics and synthetic process of mSWCNT-FITC. A: AFM image of mSWCNT; B: AFM height analysis (about 30 nm) of mSWCNTs in image A; C: TEM image of mSWCNT: D: mSWCNT-FITC covalent linking process

Nickel nanoparticles remained on the surface or are trapped inside SWCNTs after purification (black dots in FIG. 20C), which indicates that these nanotubes are magnetic SWCNTs (mSWCNTs). After purification, these mSW-CNTs still exist in bundles with diameters ranging from about 20-40 nm (FIGS. 20A, 20B), which suggests at least 10 SWCNTs are bundled together because the diameter of a single SWCNT is about 2-3 nm. FIG. 20D shows the synthetic process for making mSWCNT-FITC. The mSW-CNTs are linked with FITC covalently through the linkage of ethyl diamine, and this covalent bond ensured that during the mSWCNT delivery process, FITC molecules and mSW-CNTs are not separated.

Figure 21:
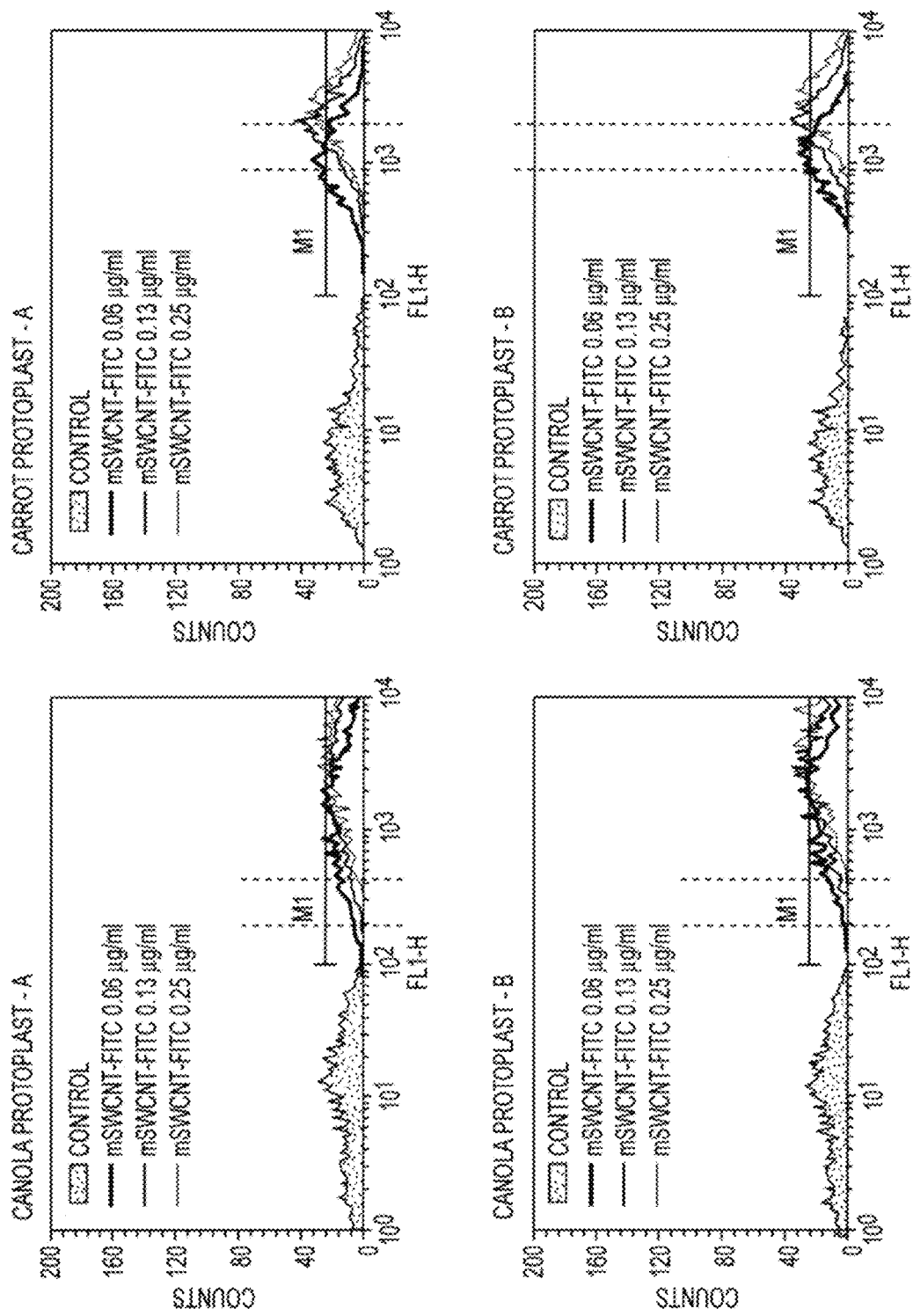
FIG. 21 shows FITC delivery efficiency (FACS results) of mSWCNT-FITC before and after 70% ethanol washing. A: 70% ethanol and PBS washing; B: PBS washing only.

According to FIG. 21, based on the FACS analysis results, FITC delivery efficiency is about 100% for both canola and carrot protoplasts when mSWCNT concentration is in the range of 0.06-0.25 µg/ml. For both canola and carrot protoplasts, a higher concentration of mSWCNTs results in a stronger fluorescence signal. This result shows that higher mSWCNT concentration corresponds to more mSWCNT-FITC entering cells. In order to ensure the mSWCNT-FITC which is attached to the surface of cells is completely removed, the protoplasts are washed twice using 70% ethanol after washing twice with PBS. In FIG. 21B, the protoplasts are washed twice only using PBS. Compared with the FACS results in FIG. 21B, after washing with ethanol, there is a small left shift for canola protoplasts and a larger left shift for carrot protoplasts are observed (FIG. 21A), which indicates most mSWCNT-FITC outside of the cells are washed away because SWCNTs are more soluble in ethanol than in water. The distributive curves of cell counts from the controls in FACS are different from that of normal mammalian cell lines. For instance, the fluorescent strength of normal mammalian cell lines is on the order of $10^0$-$10^1$, but those of the two protoplasts tested are on the order of $10^0$-$10^2$, which indicated some of the fluorescent signal is from the protoplasts.

It is hypothesized that these results mainly come from the remaining cell walls that the enzyme used could not completely remove. In fact, this assumption is confirmed by fluorescent microscope because some fluorescent signals from the cell walls of canola cells can be observed. Although the fluorescent signal from the cell walls interferes with the FACS results, it is still seen that all fluorescent signals becomes stronger after mSWCNT-FITC delivery. It seems that mSWCNT-FITC penetrates the cells with or without the cell wall because if no mSWCNT-FITC would have entered into the walled cells, the fluorescent signals of these walled cells would remain un-shifted.

Figure 22:
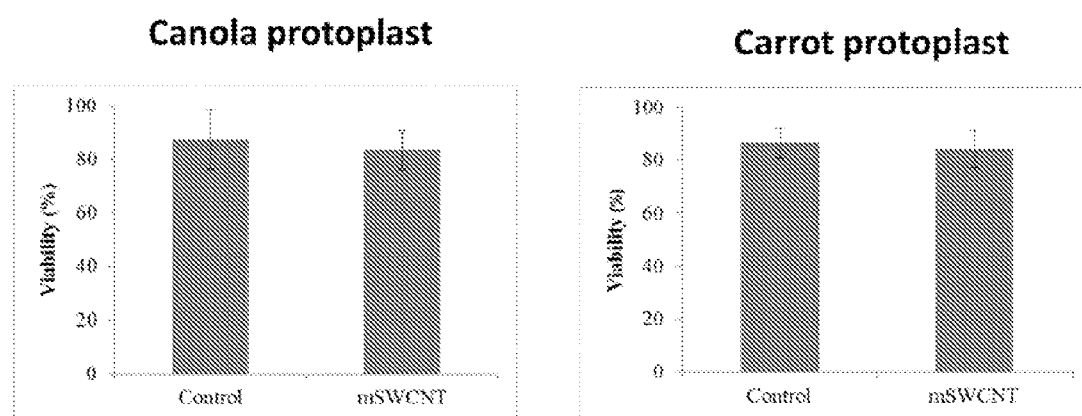
FIG. 22 shows Canola and carrot protoplast viability treated with mSWCNT-FITC.

FIG. 22 shows that mSWCNTs are not cytotoxic for the canola and carrot protoplasts because the cell viability after treatment with mSWCNT-FITC remained similar to the control.

Figure 23:
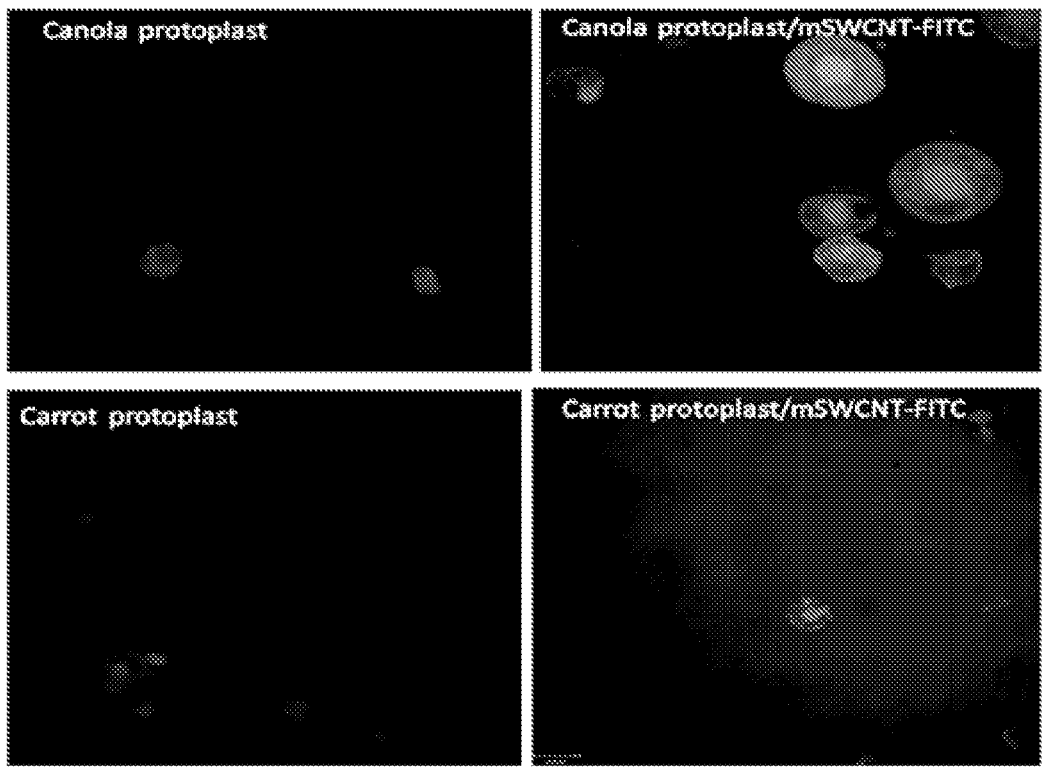
FIG. 23 shows confocal images of canola and carrot protoplasts/mSWCNT-FITC. (Because the size of carrot cell is much smaller than that of canola cell, the green fluorescent signal in carrot cell is weaker than the canola cell.)
Figure 24:
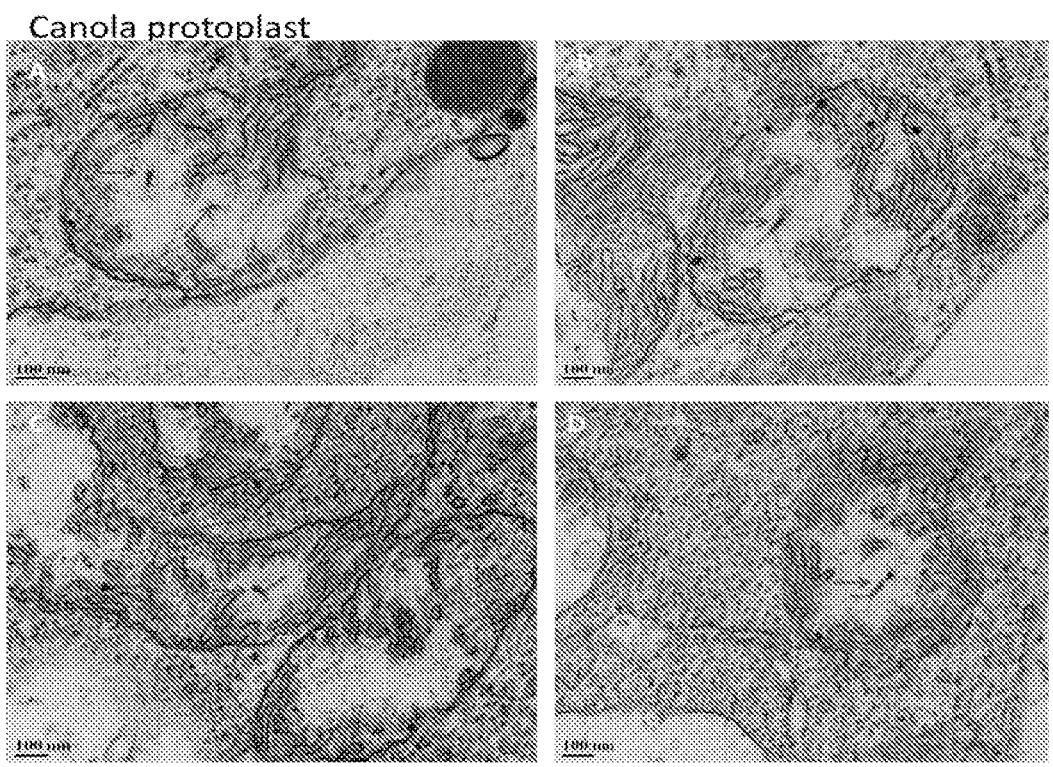
FIG. 24 shows sectional TEM images of canola and carrot protoplasts/mSWCNT-FITC.

In order to confirm our observations, confocal and sectional TEM imaging of these two protoplasts is performed. Compared to the control cells, green fluorescent signals appears in most cells after mSWCNT-FITC delivery. The signal strength is different for different cells, which reflects how much FITC enters the cells (FIG. 23). Even though the carrot protoplasts are smaller than the canola protoplasts, the mSWCNT-FITC is also able to enter them. There are some green fluorescent signals which appears near the nucleus, which means that the FITC is near the nucleus. FIG. 24 is the sectional TEM images of these two protoplasts. For canola protoplasts, the mSWCNTs are found in endosomes (FIG. 24—canola A, B, C, D). However, for carrot protoplasts, an mSWCNT is found outside the cell and an mSWCNT is found near nuclear membrane. All these results show that mSWCNTs not only enters cells but also distributes in different organelles inside plant cells.

To ensure the delivery of FITC, it is covalently bound with mSWCNTs. FACS results show that mSWCNT-FITC can enter canola and carrot protoplasts driven by an external magnetic force. The FITC delivery efficiency is about 100% according to FACS results. Confocal and sectional TEM images further confirm that mSWCNT-FITCs are inside these plant cells. mSWCNTs are also found both in the endosomes of canola protoplasts and outside endosomes near the nuclear membrane of carrot protoplasts.

Example 11—Magnetic Gold Nanoparticles: Synthesis, Characterization and its Application in the Delivery of FITC into KG-1 Cells Materials and Methods
Chemicals:

The sodium citrate trihydrate, chloroauric acid, ascorbic acid, fluorescein isothiocyanate (FITC), dimethylformamide (DMF) and sodium dodecyl sulfate (SDS) used in this study are from Sigma-Aldrich. Iscove's Modified Dulbecco's Medium (IMDM), Fetal Bovine Serum and Penicillin/streptomycin used are from GIBCO. Thiol polyethylene glycol (PEG) with amino functional group is purchased from NANOCS company with molecular weight 5000.

Cells:

KG-1, acute human leukemia cell lines are purchased from the American Type Culture Collection (ATCC HTB22, Rockville, Md. USA).

Synthesis of Magnetic Gold Nanoparticles (mGNPs):

The following procedures outline the synthesis of mGNPs. (1) Synthesis of iron nanoparticles: 2.78 g of Iron(II) sulfate heptahydrate and 3.25 g of Iron (III) chloride hexahydrate are transferred into to a clean 125 mL conical flask containing 25 mL of MilliQ high purity de-ionized water. 0.85 mL of concentrated HCl is transferred into the flask. This solution is added dropwise into 250 mL of 1.0 N NaOH solution until a black solution is obtained. 400 µL of the black solution is diluted to 80 mL using MilliQ high purity de-ionized water, and is sonicated for 2 hours. (2) Synthesis of mGNPs: 1 mL of 25 mM chloroauric acid and 2 mL of 20% sodium dodecyl sulfate solution (SDS) are transferred to a clean 20 mL vial containing 16 mL of MilliQ high purity de-ionized water. 1 mL of iron nanoparticle solution prepared above and 300 µL of the above $HAuCl_4$ solution are transferred into a 20 mL vial. The vial is sonicated for 15 min. Meanwhile, a solution of ascorbic acid (AA) is prepared by dissolving 0.0400 g of AA powder in 20 mL of MilliQ water. 180 µL of AA solution is transferred into the vial and stirred for 30 min. 200 µL of 10% HCl solution is transferred into this vial and stirred for an additional 30 min.

Synthesis of mGNP-FITC:

(1) 0.0116 g HS-PEG-NH2 (MW 5000) is dissolved into a 20 mL vial containing 10 mL of MilliQ water. 1 mL of the above mGNP solution is transferred into this vial and stirred for 5 min. This vial is kept at 4° C. overnight. (2) The solution is centrifuged at 10000 rpm for 30 min. The supernatant is discarded and the sediment is washed once using the same centrifuge conditions. The sediment is dissolved in 0.5 mL of MilliQ water (mGNP solution). Meanwhile, 100 mg FITC is dissolved into 0.5 mL of DMF, and then mixed with above mGNP solution. The mixture is stirred for 5 minutes before being kept at room temperature overnight. The mixture is dialyzed until no free FITC in solution remained.

Cell Culture and Magnetic-Field-Driven Cellular Uptake Experiment

KG-1 cells with a density of $5 \times 10^5$ cells per plate are placed in poly-L-lysine (10 µg $mL^{-1}$)-coated 35 mm culture dishes and incubated for 45 min at 37° C., 5% $CO_2$. The magnetic-field-driven delivery method is to place a culture dish containing 1 mL IMDM media with 18.8 nmol Au $mL^{-1}$ of mGNP-FITC or mGNP on the top of an Nd—Fe—B permanent magnet for 2-6 hrs, then the culture dish is put back in incubator overnight. The uptake experiment is terminated by washing the cells with PBS buffer.

MTS Experiment:

(1) 30,000 cells are seeded per well in 96-well plates. The experiment is conducted in quadruplicate. (2) mGNP stock solution is diluted in growth medium to concentrations of 4.7, 9.4, 18.8, 37.5, and 75 nmol Au $mL^{-1}$. (3) 200 µL of mGNP-FITC containing growth medium is added per well and the 96-well plates are put back into the incubator to continue culture for 24 and 48 hrs. (4) 20 µL of MTS solution is added (5 mg mL-1 in 1×DPBS), then the cells are incubated for additional 3 hrs. (5) Absorbance at 490 nm is measured.

Flow Cytometry Measurement:

KG-1 cells exposed to mGNP-FITC for different amounts of time on magnets are collected and centrifuged at 1200 rpm for 10 min. The collected cells are extensively washed using PBS and then fixed in 1% paraformaldehyde and resuspended in 400 µL of PBS. The mGNP-FITC delivery efficiency is evaluated with Flow Cytometry (FACscan, Becton-Dickinson, San Jose, Calif., USA) at an excitation wavelength of 488 nm.

Atomic Force Microscope (AFM) Image:

A small amount of sample solution is directly transferred dropwise onto a silicon wafer. The sample is covered and kept at room temperature until the solution is dry. AFM images are taken using Veeco Multimode V SPM operating in tapping mode.

Fluorescent Microscopy:

The fluorescent images are taken by using Fluorescent Microscopy of Leica CW 225 A with Nikon digital camera DXM1200.

Confocal Microscope Images:

KG-1 cells are seeded at a density of $1 \times 10^5$ cells $cm^{-2}$ on cover slips previously coated with poly-L-lysine (10 µg $mL^{-1}$) for 45 min at 37° C., 5% $CO^2$. The cells are exposed to 18.8 nmol Au $mL^{-1}$ mGNP-FITC and mGNP (the control)

on an Nd—Fe—B permanent magnet. Uptake is terminated by washing the cells twice with ice-cold PBS. After 4 hrs of incubation on an Nd—Fe—B permanent magnet, the cells is incubated in an incubator for an additional 12 hours, then fixed in 2% paraformaldehyde, stained and examined under a confocal laser scanning microscope (Quorum Wave FX-Sinning Disk) equipped with imaging software—Hamamatsu EMCCD (C9100-13).

TEM Image:

The TEM images are taken using Philips-FEI Morgagni 268 instrument, and operated at 80 kV. The sample solution is deposited on the copper support coating with carbon.

Synthesis of mGNPs

Figure 25:
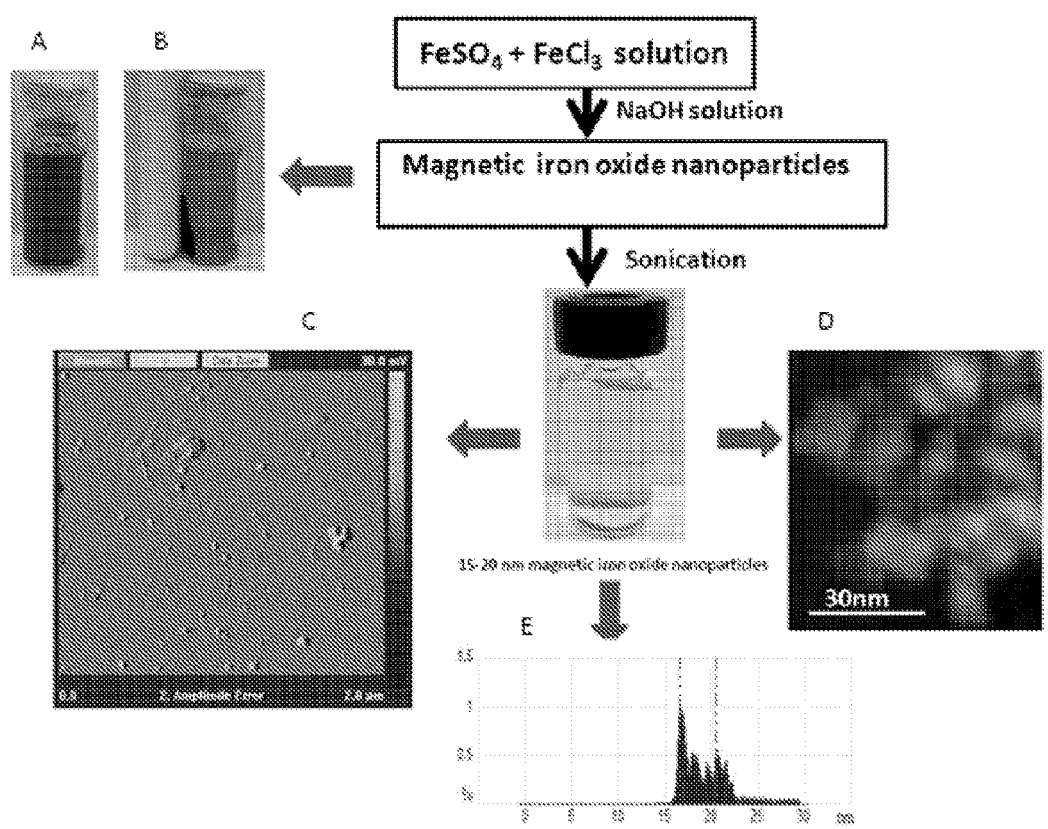
FIG. 25 shows the synthesis of iron oxide nanoparticles. (A) Solution of magnetic iron oxide nanoparticles. (B) Solution of magnetic iron oxide nanoparticles beside a magnet. We can clearly see the nanoparticles were driven towards the magnet side. (C) AFM image of 15-20 nm magnetic iron oxide nanoparticles. (D) TEM-scan image of 15-20 nm magnetic iron oxide nanoparticles. (E) AFM analysis showing the vertical height (15 to 20 nm) of the nanoparticles in image C.
Figure 26:
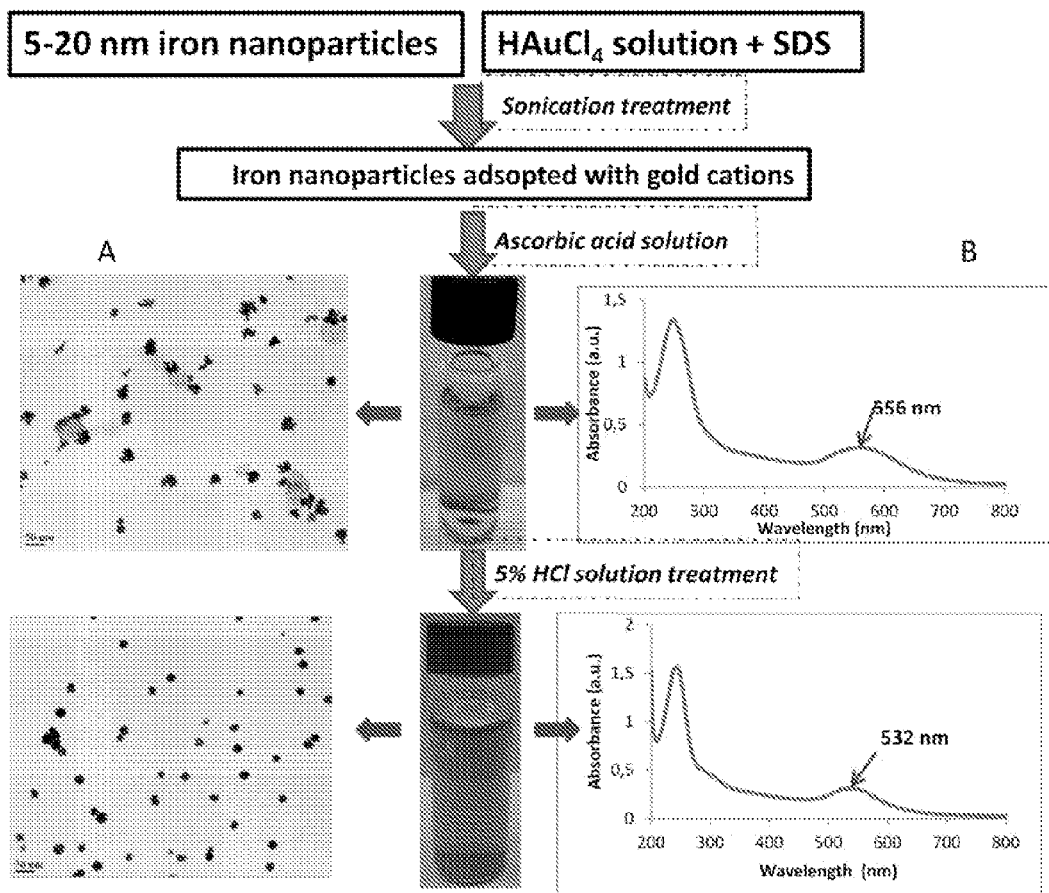
FIG. 26 shows synthesis of mGNPs: (A) TEM image of mGNPs with a purple color. (B) UV-Vis spectrum of mGNPs with a purple color. (C) TEM image of mGNPs with a red color (D) UV-Vis spectrum of mGNPs with a red color.
Figure 27:
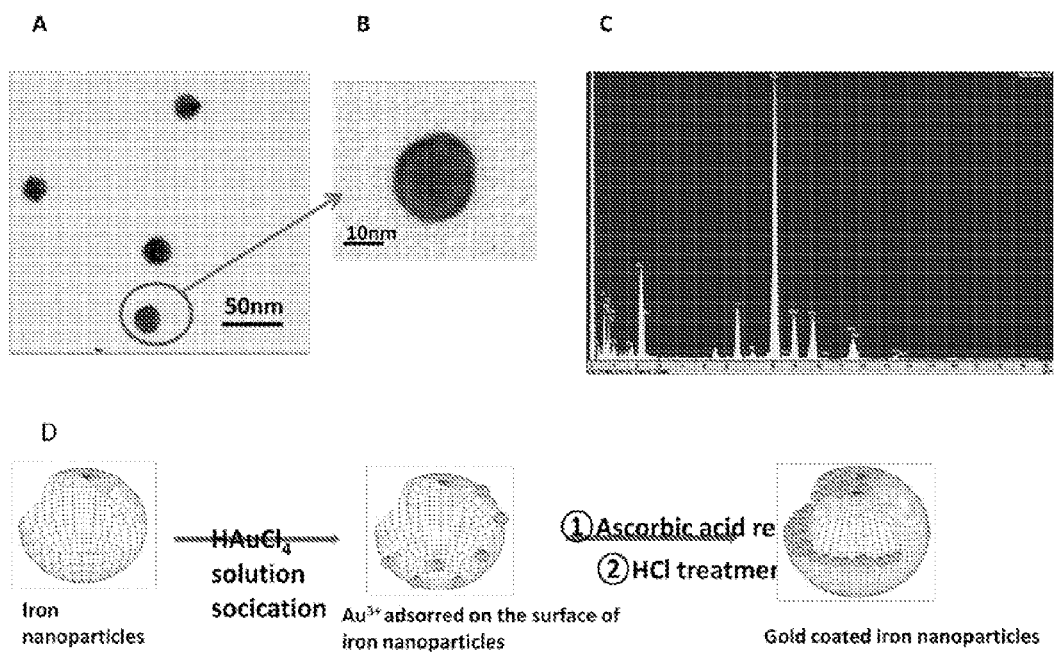
FIG. 27 shows core-shell structure of mGNPs. (A) TEM image of mGNPs. (B) Zoomed-in image of an mGNP. (C) EDX analysis of the image in B. (D) Scheme—formation of core-shell mGNP structure.

The synthesis of mGNPs consists of two steps. The first step is to synthesize iron oxide nanoparticles with suitable size. FIG. 25 shows the design process and characterization of the iron oxide nanoparticles, and we followed this typical method to synthesize iron oxide nanoparticles. The color of the iron oxide nanoparticle solution is black (FIG. 25A). When a magnet is put beside the solution, the iron oxide nanoparticles quickly move towards the magnet (FIG. 25B), which confirms the magnetism of the iron oxide nanoparticles. The iron oxide nanoparticles are big enough that their migrated towards magnet is visually observable. However, their size is too big for the creation of mGNPs, and smaller particles have to be prepared. This problem can be solved by using sonication. After sonication treatment, the black-colored solution of magnetic iron oxide nanoparticles becomes light yellow (in the middle of FIG. 25). According to AFM and TEM images (FIGS. 25C and 25D), the size of iron oxide nanoparticles is about 15-20 nm. The morphology is uneven. AFM analysis of the vertical height of the particles also gave a similar result (FIG. 25E). The second step is to synthesize mGNPs. The synthesis of these mGNPs is shown in FIG. 26. By sonicating the mixture of $HAuCl_4$, surfactant SDS (sodium dodecyl sulfate) and the 15-20 nm iron oxide nanoparticles, the gold cations are adsorbed on the surface or trapped inside the micropores of the iron oxide nanoparticles. After quick reduction, the gold cations becomes gold nanoparticles and aggregated together due to the instability of nanoparticles. Some aggregated gold nanoparticles form a shell outside the iron oxide nanoparticles; some aggregated together surrounding iron oxide nanoparticles (FIG. 25A). The solution is purple and the absorbance in the UV-Vis spectrum is at 556 nm, which indicates the nanoparticles are bigger (FIG. 25B). The size indicated using this UV-Vis spectrum method should reflect the mean size of the gold, iron oxide and their aggregation. After the purple solution is treated using a 5% HCl solution, the solution became red and the absorbance in UV-Vis spectrum is at 532 nm, which indicates that the nanoparticles are about 20-30 nm in size (FIG. 25D) according to the normal UV spectrum character of gold nanoparticles. During this treatment, the iron oxide outside the nanoparticles are dissolved and removed; only the iron oxide inside the nanoparticles remains. Therefore, the cluster of iron oxide and gold nanoparticles is broken, the aggregation of nanoparticles becomes dispersed into smaller nanoparticles. Because the metallic gold is formed on the surface or inside the micropores of iron oxide nanoparticles, the only iron oxide remaining must have been inside gold nanoparticles. The morphology and size of mGNPs became consistent (FIG. 26C). The ideal configuration would be for the metallic gold aggregated to form a shell around the surface of iron oxide nanoparticles. This structure is confirmed by the zoomed-in image (FIG. 27A, B). The core-shell structure of the mGNP can be clearly seen. There is a relative black shell and relative gray core. Because the contrasts of gold and iron are different in TEM image and the contrast of gold is larger, the black shell in this zoomed-in image should belong to gold and relative gray core should belong to iron oxide. Due to the spherical structure, there is a small amount of darker coloring in relative gray core produced by outside gold. The EDX analysis in FIG. 27C shows that the nanoparticles are composed of Fe and Au, which verified the core-shell structure. The schematic of the core-shell structure forming process for the mGNPs is shown in FIG. 27D.

FITC Delivery into KG-1 Cell Line Using mGNPs

Figure 28:
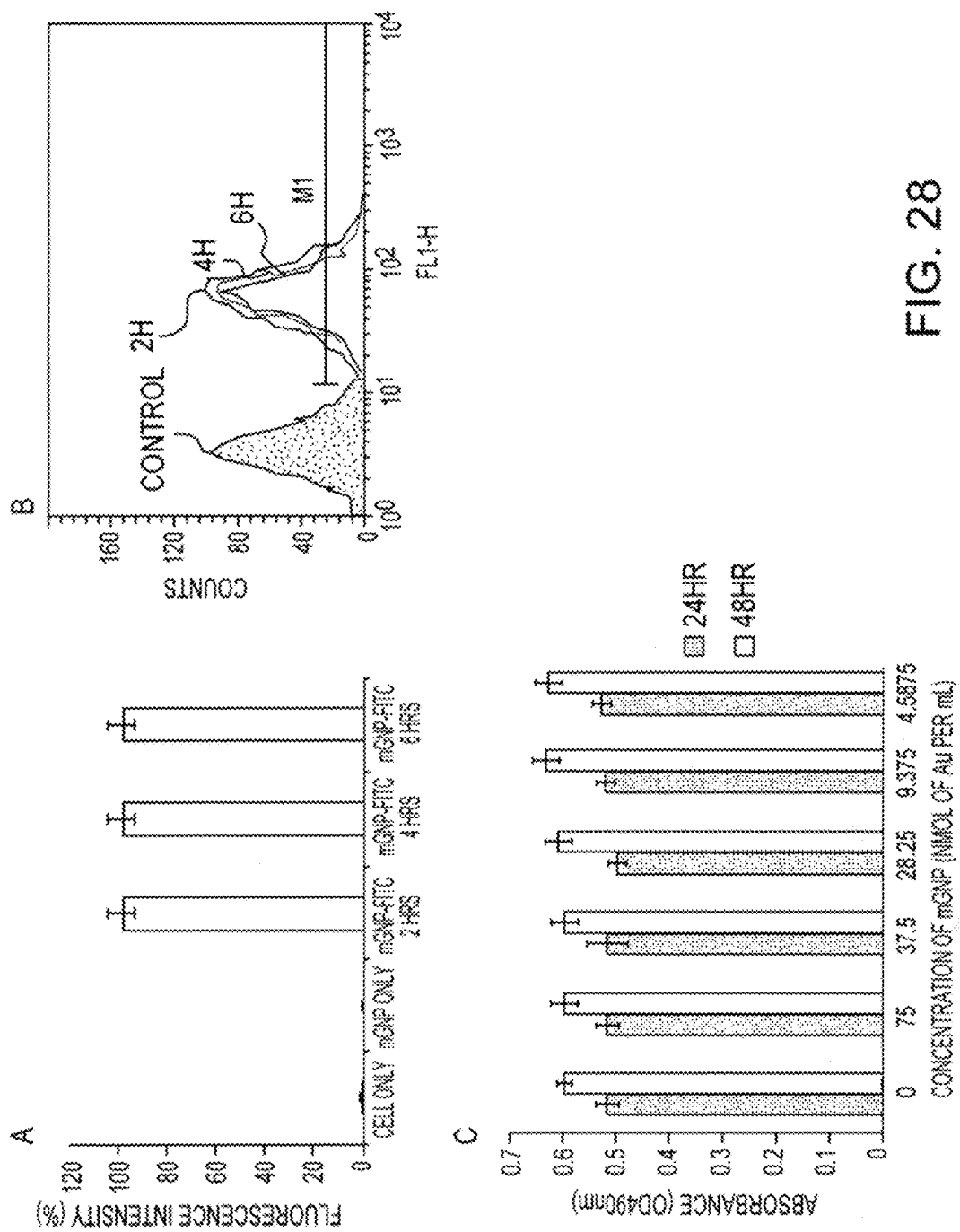
FIG. 28 shows cytotoxicity of mGNP and FACS results of mGNP-FITC delivery. (A) KG-1 cell uptake efficiency for mGNP-FITC; (B) Uptake efficiency comparison of different standing time on Magnet (Purple: control; green: 2 hrs; red: 4 hrs; blue: 6 hrs); (C) Cytotoxicity of mGNP from MTS method.
Figure 30:
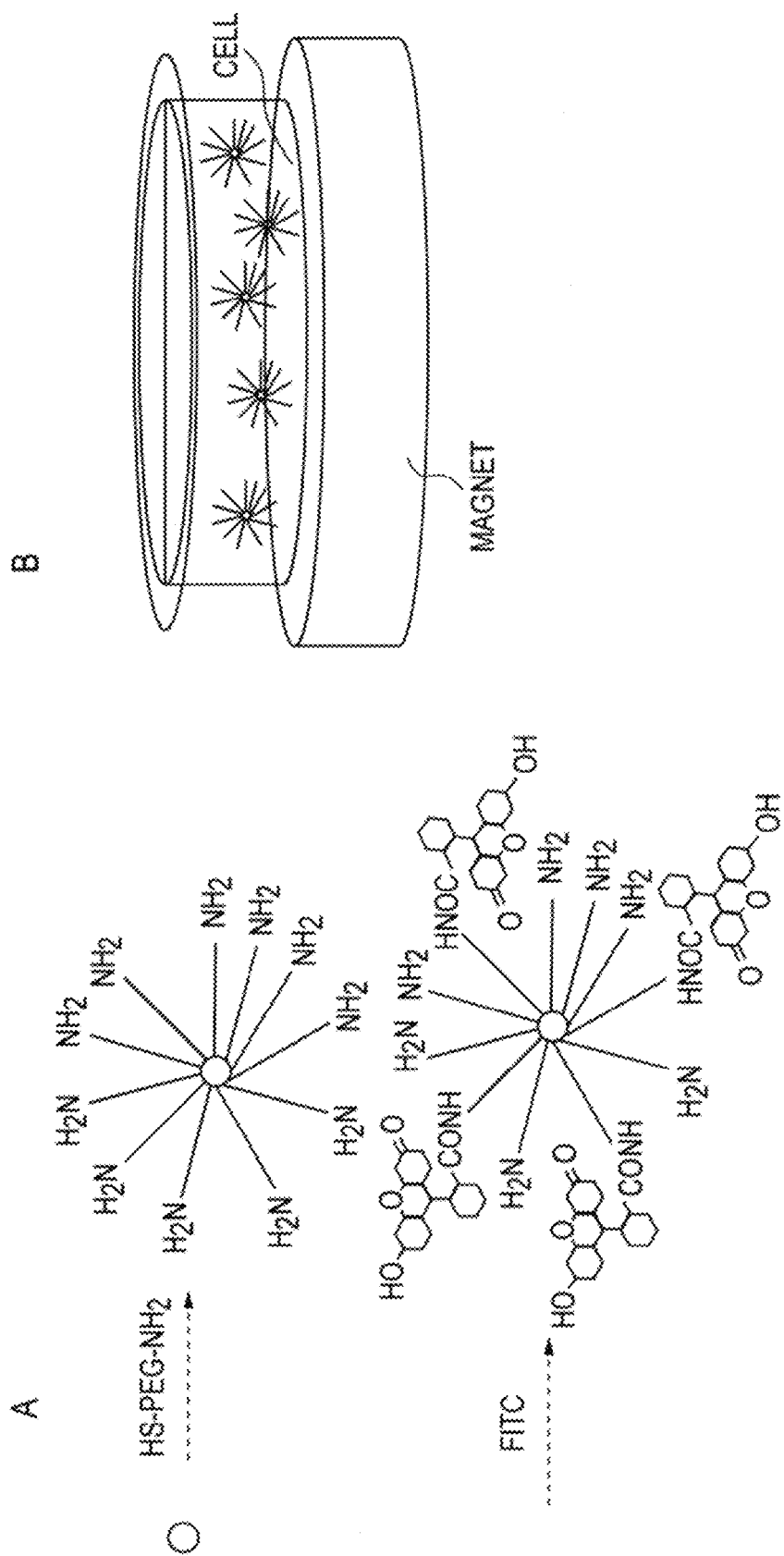
FIG. 30 shows synthesis of mGNP-FITC and cell uptake for mGNP-FITC. (A) Synthetic process (B) Cell uptake for mGNP-FITC.

FIG. 30A shows the linking process between mGNP and FITC molecules; and FIG. 30B shows the cellular uptake experiment design of delivering FITC into KG-1 cells driven by an external magnetic force. By taking advantage of the gold covering the magnetic nanoparticles, PEG can be covalently bound with mGNPs because thiol-PEG with amino functional groups can interact with gold through thiol functional groups. An FITC molecule can react with an amino functional group to form a covalent bond through an amide (FIG. 30A). Therefore, through PEG bridges, FITC molecules can link to the surface of mGNPs through covalent bonds which can avoid the FITC lost during uptake process. Due to the solubility of PEG, mGNP-FITC can dissolve in the culture medium of the KG-1 cell line to form a uniform solution. Therefore, after the cellular uptake experiment, most of the mGNP-FITC left on cell surfaces can be removed by completely washing the cells twice using PBS buffer, then the fluorescent signals in FACS measurement should only come from the mGNP-FITC inside KG-1 cells. When the KG-1 cells with mGNP-FITC in culture medium are put on top of the magnet, the mGNP-FITC moves towards the bottom of culture dish and is adsorbed on the surface of KG-1 cells. These mGNP-FITCs may continue to move into cells due to the magnetic force and may have been engulfed by the cells themselves (FIG. 30B). The FACS results shows that standing for two hours on the magnet is enough for FITC delivery into cells driven by magnetic forces because no identifiable difference is observed for standing on the magnet for 2, 4 and 6 hours (FIG. 28A,B). The FITC delivery efficiency is about 100% for standing for 2, 4 and 6 hours. FIG. 28C shows no cytotoxicity for mGNPs for both 24 and 48 hours among concentrations ranging from 4.7-75 nmol Au mL-1 using the MTS method.

Figure 29:
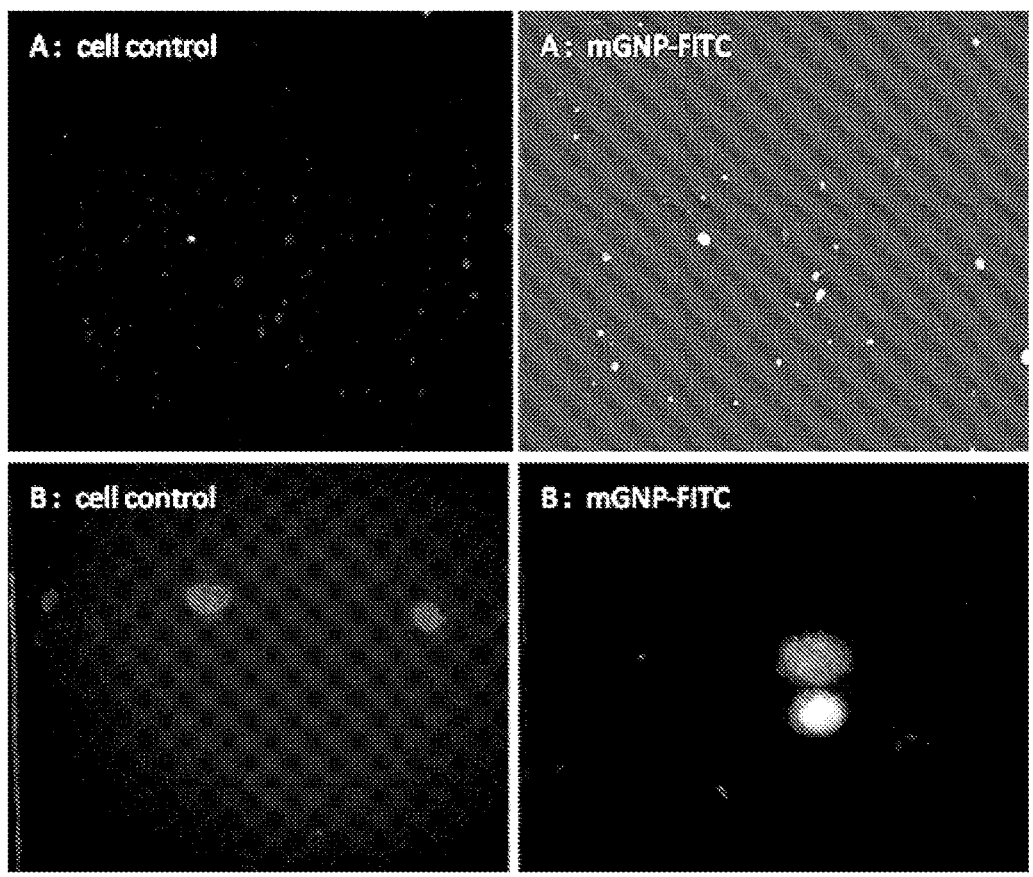
FIG. 29 shows images of Fluorescent microscope and confocal for KG-1 cell treated with mGNP-FITC. (A) fluorescent microscope (×100), (B) confocal microscope.

In order to confirm the results of the FITC delivery into the KG-1 cell line, images from both fluorescent and confocal microscopy are taken (FIG. 29). Compared with the blue channel (checking cell nucleus), the image (FIG. 29A) in the green channel (fluorescent signal) of fluorescent microscopy showed that not all KG-1 cells took up the mGNP-FITCs even though the FITC delivery efficiency is about 100% according to FACS results. This error may have arisen due to the limitations of the analytic methods of the FACS instrument. According to the confocal image in FIG. 29B, we can clearly see that the green fluorescent signal surrounded the nucleus of the cells, there are some especially highlighted spots near the nucleus, which confirmed that mGNP-FITCs actually entered into KG-1 cells and migrated towards cell nucleus.

Sonication can disperse iron oxide nanoparticles into smaller nanoparticles and also make gold cations adsorb on the surface or become trapped in the micropores of the iron oxide nanoparticles. Through a quick reduction of ascorbic acid and post-HCl solution treatment, mGNPs with a uniform spherical morphology and sizes around 20-30 nm can be synthesized in a water solution. The mGNPs have a core-shell structure. mGNPs are non-cytotoxic and mGNP-FITCs can enter into the KG-1 cell line, which is confirmed by the confocal images.

Example 12—FITC Delivery into Plant Cells with and without Cell Walls Using Magnetic Gold Nanoparticles Cell culture: MD cell suspensions of canola (*B. napus* L. var. *Jet Neuf*) are maintained on a rotary shaker (160 rpm) at 20° C. in NLN media (pH6.0, containing 6.5% sucrose, 30 mg/L glutathione, 800 mg/L glutamine, 100 mg/L Lserine, 0.5 mg/L a-naphthaleneacetic acid (NAA), 0.05 mg/L 6-benzylaminopurine (BA) and 0.5 mg/L 2,4-D). At 2-week intervals, one third of the mass of cells grown in 125 mL flasks is transferred to 50 mL of fresh NLN medium. Seeds of carrot (*D. carota* L. var. *Konservnaja* 63) are obtained from Plant Gene Resources of Canada (Saskatoon, Saskatchewan). Cells derived from leaves of in vitro plants are cultured in MS media, 3% sucrose, 0.2 mg/L BA, 1.0 mg/L NAA (pH=6). Two to Three days after subculture, cells are used for protoplast isolation.

Protoplast Isolation:

Plant cells are preplasmolyzed by incubation in CPW13M solution for 1 hour at room temperature. The solution is then replaced with a digestion solution, consisting of ½ MS salts, 0.06% 2-(N-Morpholino)ethanesulfonic acid (MES), 13% mannitol, 0.1% Macerozyme R-10 (Yakult Honsha Co., Japan) and 0.5% Cellulase Onozuka R-10 (Yakult Honsha Co., Japan), pH 5.8. The incubation is carried out overnight (16 hrs) at 25° C. in the dark. The digestion mixture is filtered through a sterile nylon cell strainer (40 µm, BD Falcon, USA) to remove the debris, and then centrifuged (100×g) for 10 min. The pellet is resuspended in CPW25S and 2 mL of CPW13M is added to the top. The protoplasts are then collected with sterilized Pasteur pipettes following centrifugation (100×g) for 10 min, washed twice, and finally resuspended in ½ NLN medium supplemented with 13% mannitol. The protoplast solution is used for the mGNP-FITC delivery experiment.

Synthesis of mGNP-FITC:

(1) 0.0116 g HS-PEG-NH2 (MW 5000) is dissolved into a 20 mL vial containing 10 mL of MilliQ water. 1 mL of the prepared mGNP solution is transferred into this vial and stirred for 5 min. The vial is kept at 4° C. overnight. (2) The solution is centrifuged at 10000 rpm for 30 min. The supernatant is discarded and the sediment is washed once using the same centrifuge conditions. The sediment is dissolved in 0.5 mL of MilliQ water (mGNP solution). Meanwhile, 100 mg FITC is dissolved into 0.5 mL DMF, then mixed with the above mGNP solution. The mixture is stirred for 5 minutes, then kept in room temperature overnight. The mixture is dialyzed until there is no free FITC in solution.

Magnetic-Field-Driven Cellular Uptake Experiment:

Protoplasts with a density of $5 \times 10^5$ cells/plate are placed in 35 mm culture dishes, the dishes are sealed with parafilm. The magnetic-field-driven delivery method is carried out by placing the culture dishes containing 1 mL of medium with 0.25 µg/mL mGNP-FITC or mGNP on the top of an Nd—Fe—B permanent magnet for 12 hrs. The protoplasts are then collected, fixed in 2% paraformaldehyde and completely washed twice with PBS and 70% ethanol, respectively.

Cell Viability:

Protoplasts are seeded in 35 mm Petri dishes in culture medium. 30 µL of mGNPs is added into each dish. The Petri dishes are put on top of the magnet at room temperature overnight. A drop of cell solution is deposited on a microscope glass slide and stained with FDA. Images are taken with both bright and green channel under a fluorescent microscope (Leica CW 225 A with Nikon digital camera DXM1200). The protoplast numbers are counted under bright channel and fluorescent channel. The cell viability or NPs cytotoxicity is then calculated.

Flow Cytometry Measurement:

Protoplasts exposed to mGNP-FITC at different concentrations are collected and centrifuged at 1000 rpm for 10 min. The collected cells are extensively washed using PBS then fixed in 2% paraformaldehyde and resuspended in 400 µL PBS. The mGNP-FITC delivery efficiency is evaluated with Flow Cytometry (FACscan, Becton-Dickinson, San Jose, Calif., USA) at an excitation wavelength of 488 nm.

Atomic Force Microscope (AFM) Image:

A small amount of sample solution is directly transferred dropwise onto the silicon wafer. The sample is covered and kept at room temperature until the solution is dry. AFM images are taken using Veeco Multimode V SPM operating in tapping mode.

Confocal Microscopy Imaging of Plant Cells:

Protoplasts are seeded at a density of $1 \times 10^5$ cells/cm$^2$ on cover slips previously coated with poly-L-lysine (10 µg/mL) for 45 min. The protoplasts are exposed to 0.25 µg/mL mGNP-FITC and mGNP (the control) on an Nd—Fe—B permanent magnet. Uptake is terminated by washing the cells twice with PBS buffer and twice with 70% ethanol, separately. After 12 hours of incubation on an Nd—Fe—B permanent magnet, the cells are fixed in 2% paraformaldehyde and examined under a confocal laser scanning microscope (Quorum Wave FX-Sinning Disk) equipped with imaging software—Hamamatsu EMCCD (C9100-13).

TEM Image:

TEM images are taken using a Philips-FEI Morgani 268 instrument, operated at 80 kV. The sample solution is deposited on the copper support, which is coated with carbon. Protoplasts are fixed in 2% glutaraldehyde in 4% PEN cacodylate buffer, pH 7.2, for 2 hours at room temperature. (a) The fixative solution is drained off and replaced with 0.1 M PBS buffer. Two further changes are done 10 minutes apart. (b) The buffer is drained and the sample is post-fixed with 1% osmium tetroxide (OSO$_4$ in 0.12 M Cacodylate buffer, pH 7.2) for one hour. (c) The sample is washed using 0.1 M phosphate buffer 3 times for a total of one half hour. (d) The sample is dehydrated through a graded ethanol series as follows: 50%, 70%, 90%, 100×3 changes; one change every 15 minutes. (e) The ethanol is drained from specimen and new ethanol: Spurr mix is added for 3 hours. The ethanol: Spurr mix is replaced with pure Spurr resin. The Petri dish is sealed overnight. (f) The Spurr resin is replaced again and the sample is dried at 70-80° C. in an oven for 18 hours. (g) The sample is cooled and then removed from molds. (h) The sample is ultracut by Reichert-Jung Ultramicrotome and stained with uranyl acetate and lead citrate.

Results and Discussion

Synthesis of mGNP-FITC

Figure 31:
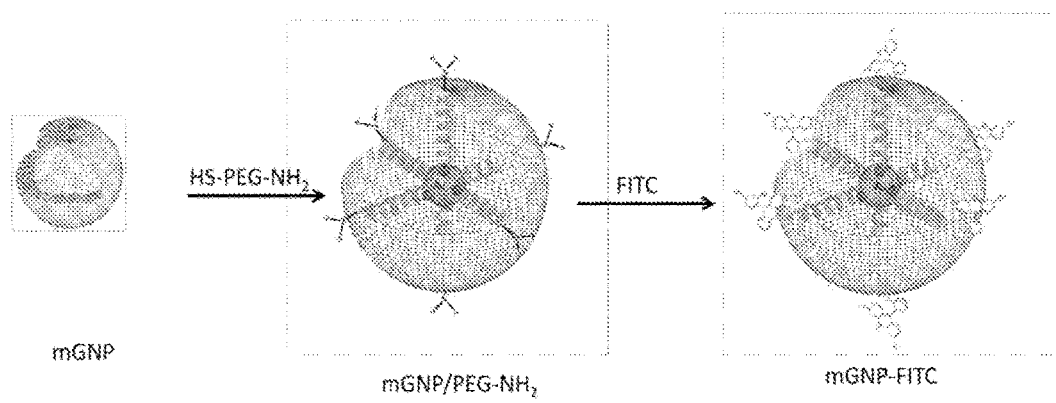
FIG. 31 shows the synthesis procedures of mGNP-FITC

Core-shell mGNPs are used to covalently bind FITC (FIG. 31). The mGNPs has a spherical morphology and are about 20-30 nm in size. The core-shell of the mGNPs is made of an iron oxide core covered completely by gold (15). When mGNPs are reacted with thiol PEG-NH$_2$ (MW 5000), the thiol functional groups interacted with gold while the amino group served as a free functional groups. Due to the spherical structure of mGNP, the amino groups distributed evenly around mGNP like a ball. After FITC reacted with amino groups, the FITC spherically mounted on the mGNP's surface as shown in FIG. 31.

Figure 36:
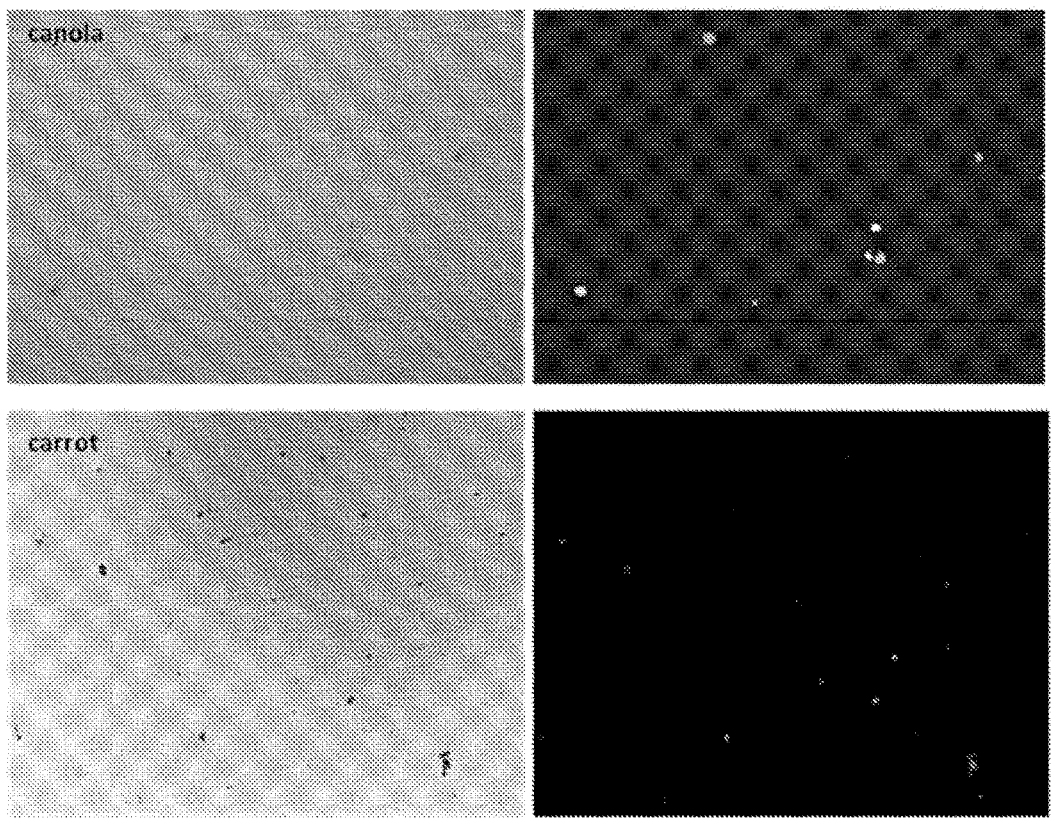
FIG. 36 shows fluorescent microscope images of canola and carrot protoplasts/mGNP-FITC (×100)

According to the FIG. 36, it can be seen that most cells in bright channel appeared in the green channel as well, which shows that most cells had green fluorescent signals as well. This result is consistent with our FACS results (FIG. 32).

FITC Delivery into Protoplasts (Plant Cells without Cell Wall)

Figure 32:
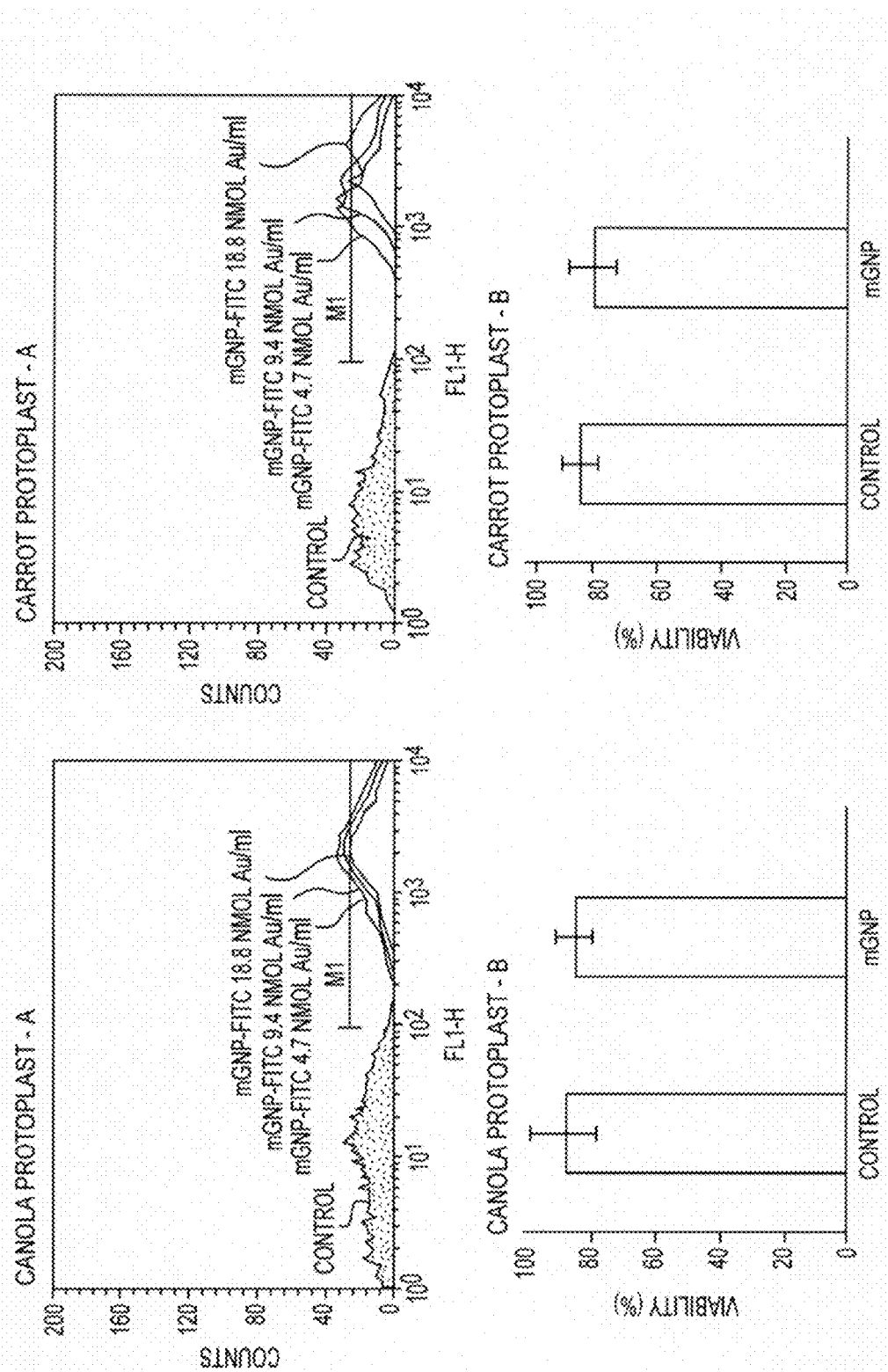
FIG. 32 shows the FITC delivery efficiency (FACS results) and cytotoxicity of mGNPs.

FACS results in FIG. 32 show that the FITC delivery efficiency is about 100% with mGNPFITC concentrations from 4.7 to 18.8 nmol Au/mL. For canola protoplasts, the difference of fluorescent strength among the three concentrations is very small (FIG. 32—Canola protoplast A), but the fluorescent strength for carrot protoplasts is quite different (FIG. 32—Carrot protoplast A). The stronger fluorescent signals reflect the higher FITC concentration. This phenomenon is caused by the different protoplast size: the size of canola protoplast is about three-times larger than that of carrot protoplast (FIG. 36). The images of fluorescent microscopy in FIG. 36 also supports our FACS results. The green fluorescent signals appears in most canola and carrot protoplasts, showing that most of mGNP-FITCs enters protoplasts. The cell count distributive curves in the control cells are different from that of normal mammalian cell lines. The fluorescent strength of normal mammalian cell lines is around $10^0$-$10^1$, but the fluorescent strengths of these two protoplasts are at $10^0$-$10^2$, which indicates that some fluorescent signals is coming from the protoplasts themselves. These results are thought to come from the remaining cell wall (the enzymatic removal of cell walls is not 100% efficient and some cell walls still remains) as some fluorescent signals from cell wall of canola cells under the fluorescent microscopy may still be observed. Even though some cell wall remains, the distributive curves of cell counts is shifted overall to the position indicating stronger fluorescent strength for both canola and carrot protoplasts after delivery using mGNP-FITC. It seems that mGNP-FITC enters into walled plant cells. FIG. 32B shows that mGNPs have no cytotoxicity because the cell viability after contacting with mGNPs is similar to that of the control cells.

Figure 33:
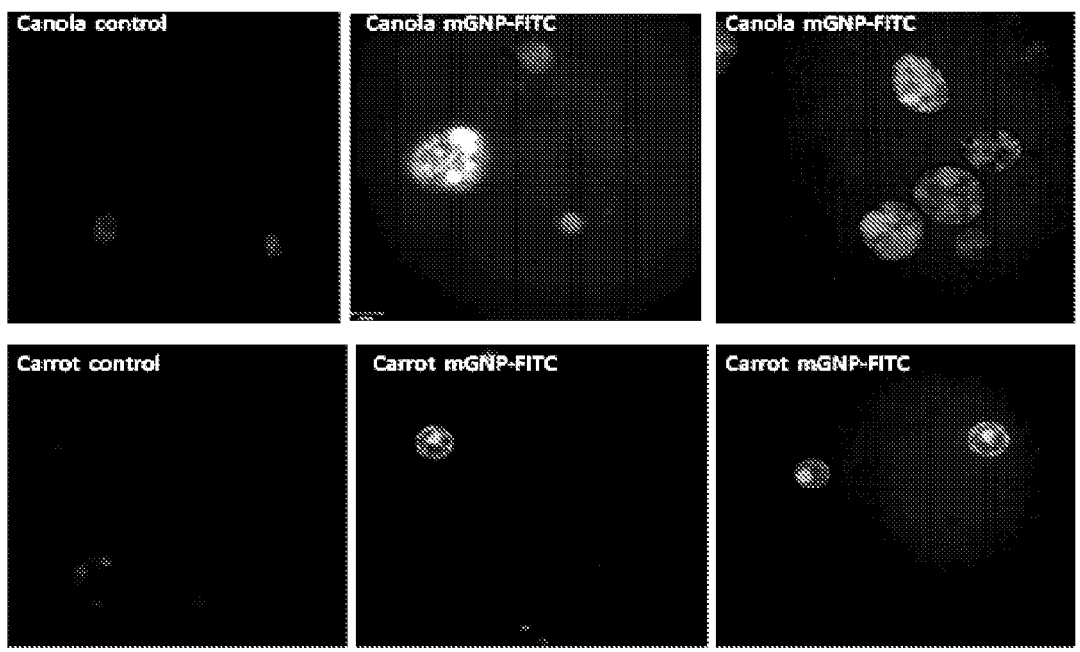
FIG. 33 shows Confocal images of canola and carrot protoplasts/mGNP-FITC.
Figure 34:
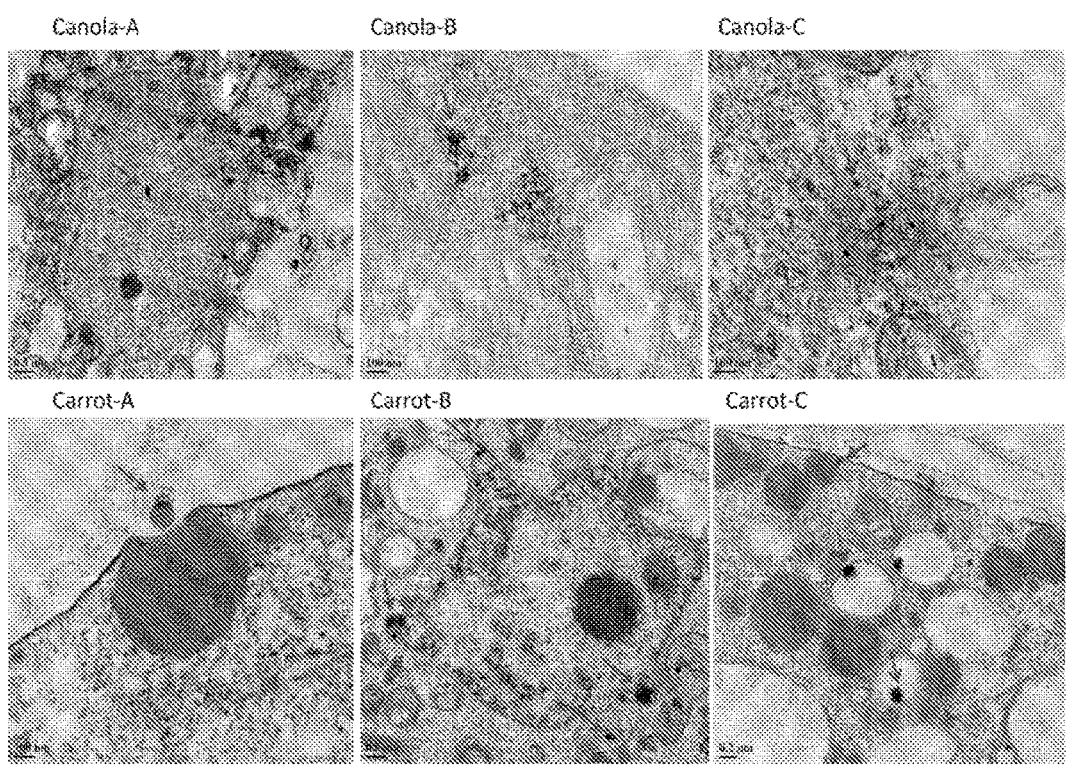
FIG. 34 shows sectional TEM images of canola and carrot protoplasts.

According to the confocal images (FIG. 33), the FITC completely enteres both canola and carrot protoplasts. Compared with control cells, strong fluorescent signals appears near the blue nuclei. For canola protoplasts, there are several small spherical green signals surrounding the blue nuclei. This result is consistent with the FITC's spherical distribution surrounding mGNPs (shown in FIG. 31). When an mGNP enters a cell, it carries all FITCs bound on the surface of mGNP, and thus shows the spherical morphology. The different mGNPs inside the cell constitutes different green fluorescent spheres. Therefore, several mGNPs must have entered the cell. The size difference in the spherical fluorescent signal is caused by the aggregation of mGNPs or different distances near the confocal section. For carrot protoplasts, this phenomenon cannot be clearly seen due to their smaller size. In order to support our hypothesis, sectional TEM imaging is also performed. A large number of mGNPs inside cells is observed. FIG. 3 shows that mGNPs exists not only inside (FIG. 34—Canola C and Carrot B) and outside the endosome (FIG. 34—Canola B, C and Carrot C) but also inside nucleus (FIG. 34—Canola A and Carrot B). According to the size analysis, most mGNPs aggregated in organelles. Because mGNPs are covered by PEG, they are stable and do not aggregate. The aggregated mGNPs show that the chemical bonds between gold and thiol functional groups may have been broken after the mGNPs entered cells. These results also show that mGNPs can carry biomolecules into cell nuclei, which provides a new method to deliver genes into plant cells because usually only genes which enter the nucleus can be expressed. FIG. 34—Carrot A shows that when an mGNP enters into the cell, an endosome is formed. Therefore, it can be hypothesize that mGNPs may enter cells through an endocytotic process. The mGNPs first enter into an endosome, then enter other organelles.

Figure 35:
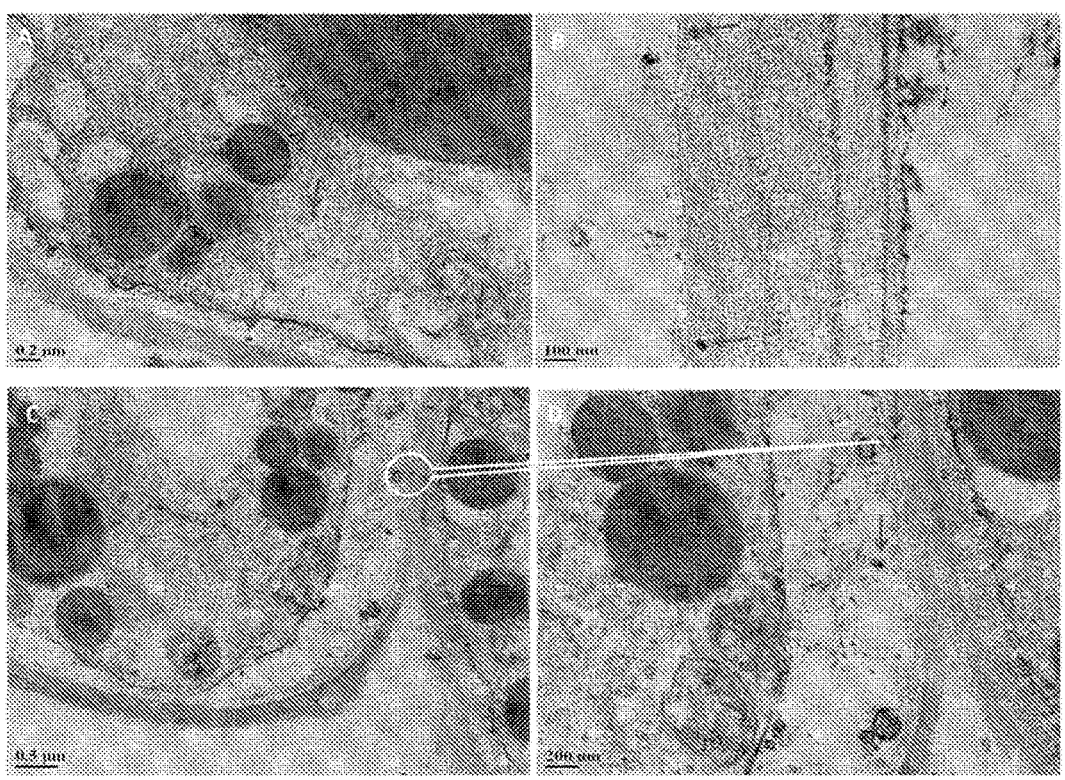
FIG. 35 shows sectional TEM images of canola intact cell.

For walled canola cells, it is found that some mGNPs went through cell wall according to the sectional TEM images (FIG. 35). In FIG. 35A, a mGNP just entered cell, near the cell wall, three mGNPs are in the cytoplasm and two mGNPs are in endosomes. In FIG. 35B, two mGNPs are going through the cell wall. According to the size and contrast analysis, these two mGNPs are carrying PEG molecules. The picture confirmed the chemical bond between FITC and mGNP did not break when the mGNP-FITC penetrated the cell wall. In FIG. 35C, two mGNPs are going through the cell wall. From the zoomed-in image (FIG. 35D), it is clearly seen that an mGNP is going through the cell wall but stopped near inside the cell wall. Combined with the results in FIG. 34, it can be concluded that, when mGNPs entered cells, the FITC remains bound with the mGNPs. When mGNPs enter other organelles, the FITC and PEG molecules may be decomposed by the enzymes and separated from the mGNPs, with the nanoparticles left in the organelles, which results in mGNP aggregation once nanoparticles became unstable.

mGNPs with uniform size and spherical morphology are covalently bonded with FITC, and are delivered into plant cells with and without cell walls driven by an external magnetic force. Two types of plant cells, canola and carrot cells, are tested. The FITC delivery efficiency is about 100% for both protoplasts according to FACS results. These results are also confirmed by the confocal and sectional TEM images. According to the sectional TEM images, mGNPs distributed in endosomes, the nucleus and the cytoplasm of canola and carrot protoplasts, but most mGNPs aggregated in organelles. The sectional TEM images also confirm that mGNPs does pass through the cell walls of canola cells, which indicated the mGNPs have the ability to directly enter walled plant cells, which is very important for plant transformation.

REFERENCES

The following references are representative of the level of skill in the art and are incorporated herein as if reproduced in their entirety (where permitted).

R. King, "Gene Delivery to Mammalian Cells by Microinjection", from book "Gene Delivery to Mammalian Cells: Volume 1: Nonviral Gene Transfer Techniques", ISBN: 978-1-58829-086-1

E. Heleniusi, M. Boije, V. Niklander-Teeri, E. Tapio Palva and T. H. Teeri, "Gene Delivery into Intact Plants Using the Helios™ Gene Gun", Plant Molecular Biology Reporter, 18: 287a-2871, 2000

V F Tendeloo, P Ponsaerts, F Lardon, G Nijs, M Lenjou, C Broeckhoven, D R Bockstaele, Z N Berneman, "Highly efficient gene delivery by mRNA electroporation in human hematopoietic cells: superiority to lipofection and passive pulsing of mRNA and to electroporation of plasmid cDNA for tumor antigen loading of dendritic cells," Blood. 2001 Jul. 1; 98(I):49-56

H Pan, Y Zhou, F Sieling, J Shi, J Cui, C Deng, "Sonoporation of Cells for Drug and Gene delivery", Engineering in Medicine and Biology Society, 2004. IEEE Conference on EMBS, Vol 2, September 2004 Page(s): 3531-3534

F Schererl, M Anton, U Schillinger, J Henke, C Bergemann, A Krüger, B Gansbacher and C Plank, "Magneto fection: enhancing and targeting gene delivery by magnetic force in vitro and in vivo", Gene Therapy, January 2002, Volume 9, Number 2, Pages 102-109

A Watson and D Latchman, "Gene Delivery into Neuronal Cells by Calcium Phosphate-Mediated Transfection", Methods, Volume 10, Issue 3, December 1996, Pages 289-291

G Beattie, E Goetzman, Q Tang, T Conlon, M Campbell-Thompson, D Matern, J Vockley, T R Flotte, "Recombinant adeno-associated virus-mediated gene delivery of long chain acyl coenzyme A dehydrogenase (LCAD) into LCAD-deficient mice", The Journal of Gene Medicine, Volume 10 Issue 10, Pages 1113-1123, August 2008

T Bettinger, R Carlisle, M Read, M Ogris, and L Seymour, "Peptide-mediated RNA delivery: a novel approach for enhanced transfection of primary and post-mitotic cells", Nucleic Acids Res. 2001 Sep. 15; 29(18): 3882-3891.

Z Liu, A Fan, K Rakhra, S Sherlock, A Goodwin, X Chen, Q Yang, D, Felsher, H Dai, "Supramolecular Stacking of Doxorubicin on Carbon Nanotubes for in vivo cancer therapy", Angew. Chem. Int. Ed., Volume 48, Issue 41, Pages: 7668-7672, Sep. 28, 2009.

M Prato; K Kostarelos; A Bianco; C D. Partidos, "Biomedical applications of functionalized carbon nanotubes", Chemical Communications, Volume 5, Pages 571-577, 2005.

Y. Sakakima, S. Hayashi, Y. Yagi, A. Hayakawa, K. Tachibana, and A. Nakao, "Gene therapy for hepatocellular carcinoma using sonoporation enhanced by contrast agents", Cancer Gene Therapy (2005), 884-889

B. Patrick, P. C. Valerie, G. Adolfo, et al. "Naked DNA Injection for liver metastases treatment in rats". Hepatology. 2002; 35:1144-1152.

Y. Yamashita, M. Shimada, K. Tachibana, et al. "In vivo gene transfer into muscle via electrro-sonoporation", Hum Gene Ther. 2002; 13:2079-2084.

M. W. Miller, D. L. Miller, and A. A. Brayman. "A review of in vitro bioeffects of inertial ultrasonic from a mechanistic perspective". Ultrasound Med. Biol. 22:1 Dil I 54, 1996

T. Leighton, "The Acoustic Bubble". Academic Press, San Diego, 1997 "Gene therapy progress and prospects: Ultrasound for gene transfer Revised and Expanded", Marcel Dekker, Inc., pp 4

D. Dalecki, S. Z. Child, C. H. Raeman, C. Cox, E. L. Carstensen, "Ultrasonically induced lung hemorrhage in young swine", Ultrasound Med Biol 1997a; 23:777-781.

P. E. Huber, P. Pfisterer, "In vitro and in vivo transfection of plasmid DNA in the Dunning prostate tumor R3327-AT1 is enhanced by focused ultrasound". Gene Ther 2000; 7:1516-1525.

H. D. Liang, Q. L. Lu, S. A. Xue, and M. Halliwell "Optimization of Ultrasound-mediated Gene Transfer (Sonoporation) in Skeletal Muscle Cells", T. Kodama, D. O. Cosgrove, H. J. Stauss, T. A. Partridge and M. J. K. Blomley, Ultrasound in Med. & Biol., Vol. 30, No. 11, pp. 1523-1529, 2004

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of magnetically transfecting animal cells in vivo or in vitro, comprising:
   directing nanoparticles through cell membranes of the cells, with magnetic force;
   wherein the nanoparticles comprise magnetic gold nanoparticles covalently attached to genetic material and/or protein,
   the nanoparticles do not comprise a viral vector,
   the nanoparticles have no or low toxicity to the cells,
   the magnetic gold nanoparticles comprise an iron oxide nanoparticle surrounded by a metallic gold shell, and
   a majority of the cells are transfected.

2. The method of claim 1, wherein the magnetic gold nanoparticles are covalently attached to the genetic material and the genetic material is DNA.

3. The method of claim 1, wherein the magnetic gold nanoparticles are covalently attached to the genetic material and the genetic material is RNA.

4. The method of claim 1, wherein the cells are mammalian cells.

5. The method of claim 1, wherein the magnetic gold nanoparticles are covalently attached to the protein.

6. The method of claim 1, wherein the magnetic gold nanoparticles have a particle size of 20-30 nm.

7. The method of claim 1, wherein the magnetic force is applied with a permanent magnet.

8. The method of claim 1, wherein the nanoparticles are biocompatible.

9. The method of claim 1, wherein the method is carried out in vitro.

10. The method of claim 1, wherein delivery efficiency is about 100%.

* * * * *